(12) United States Patent
Mao et al.

(10) Patent No.: US 8,686,223 B2
(45) Date of Patent: Apr. 1, 2014

(54) GENETIC TRANSFORMATION OF JATROPHA CURCAS

(75) Inventors: Hui Zhu Mao, Singapore (SG); Jian Ye, Singapore (SG); Nam Hai Chua, New York, NY (US)

(73) Assignee: Joil (S) Pte Ltd., Singapore (SG)

( * ) Notice: Subject to any disclaimer, the term of this patent is extended or adjusted under 35 U.S.C. 154(b) by 0 days.

(21) Appl. No.: 13/541,142

(22) Filed: Jul. 3, 2012

(65) Prior Publication Data

US 2012/0272403 A1    Oct. 25, 2012

Related U.S. Application Data

(63) Continuation of application No. 13/139,592, filed as application No. PCT/SG2009/000479 on Dec. 15, 2009, now Pat. No. 8,609,418.

(60) Provisional application No. 61/122,454, filed on Dec. 15, 2008.

(51) Int. Cl.
   - C07K 14/415    (2006.01)
   - C12N 15/10     (2006.01)
   - A61K 38/00     (2006.01)
   - C12N 15/29     (2006.01)
   - C12N 15/84     (2006.01)

(52) U.S. Cl.
   USPC ........... 800/278; 800/281; 800/294; 800/298; 435/91.1; 435/70.1; 435/320.1; 435/469; 536/23.6; 530/370

(58) Field of Classification Search
   CPC ........... C12N 15/8247; C12N 15/8261; C12N 15/8251; C12N 15/8245; C12N 15/8273; C12N 15/8271; C12N 15/8216; C12N 15/8205; C12N 15/8217; C12N 15/8218; C12N 15/8242; C12N 15/8243; C12N 15/8246; C12N 15/82; C12N 15/8203; C12N 15/8222; C12N 15/8226; C12N 15/823; C12N 15/8234; C12N 15/8235; C12N 15/8237; C12N 15/8238; C12N 15/8239; C12N 15/8253; C12N 15/8255; C12N 15/8257; C12N 15/08; A23L 1/366; A23L 1/3055; A23L 1/20; A23L 1/2005; A23L 1/3006; A23K 1/164; A23K 1/14; A23K 1/1631; A23K 1/1643; A23K 1/1813; A23K 1/1826; A23K 1/146; A01H 5/00; A01H 1/06; A01H 3/00
   See application file for complete search history.

(56) References Cited

U.S. PATENT DOCUMENTS

2008/0196121 A1    8/2008    Murali et al.

FOREIGN PATENT DOCUMENTS

| CN | 1799340 A | 7/2006 |
|---|---|---|
| EP | 1817956 A2 | 8/2007 |
| KR | 10-0856930 B1 | 9/2008 |
| KR | 100856930 B1 | 9/2008 |
| WO | 03/002751 A2 | 1/2003 |
| WO | 2008/068498 A2 | 6/2008 |

OTHER PUBLICATIONS

Kumar et al. (Industrial Crops and Products, (2010) 32: pp. 41-47).*
Berchmans et al. (Bioresource Technology, (2008), 99, 1716-1721, available online May 24, 2007).*
Sato et al. (DNA Research, 18, (2011), pp. 65-76).*
Yuan, Rui-Lang et al., "Research Progress of Tissue Culture and Rapid Propagation of Jatropha curcas," Journal of Anhui Agri. Sci., vol. 29, No. 36, Oct. 2008, abstract only in English, 4 pages.
Chinese Office Action and Search Report, Application No. 200980150544.3 dated Dec. 15, 2009, Applicant: Temasek Life Sciences Laboratory Limited, 19 pages.
Cernac, A. et al., "Wrinkled1 encodes an AP2/EREB domain protein involved in the control of storage compound biosynthesis in Arabidopsis," The Plant Journal, 2004, vol. 40, pp. 575-585, © 2004 Blackwell Publishing Ltd.
Extended European Search Report dated Sep. 17, 2012, EP Application No. 12173513.8-2403, Applicant: Temasek Life Sciences Laboratory Limited, Reference: OWK/P42736EP-D1, 10 pages.
Rajore, S. et al., "An Alternative for Regenerable Organogenic Callus Induction in Jatropha curcas L.," Indian Journal of Biotechnology, vol. 6, Oct. 1, 2007, pp. 545-548, XP007917025.
Sardana, J. et al., "An Expeditious Method for Regeneration of Somatic Embryos in Jatropha curcas L.," Phytomorphology, vol. 50, Nos. 3-4, pp. 239-242, Jan. 1, 2000, XP009144284.
Deore, A.G. et al., "High-Frequency Plant Regeneration from Leaf-Disc Cultures of Jatropha curcas L.: An Important Biodiesel Plant," Plant Biotechnology Reports, vol. 2, No. 1, Apr. 2008, pp. 7-11, XP002674111.
PhytoTechnology Laboratories, Inc., "Tissue Culture Media-Composition," Product Information Sheet, 2003, XP002674112, 7 pages.
Extended European Search Report—EP Communication dated May 29, 2012, Reference: GMW/P42736EP, Application No./Patent No. 09833762.0-2403 / 2373152 PCT/SG2009000479, Applicant: Temasek Life Sciences Laboratory Limited, 10 pages.
Sujatha, M. et al., "Role of biotechnological interventions in the improvement of castor (Ricinus communis L.) and Jatropha curcas L.," Biotechnology Advances, Oct. 2008, vol. 26(5), pp. 424-435.
Rajore, S. & Batra, A., "An alternative source for regenerable organogenic callus induction in Jatropha curcas L.," Indian Journal of Biotechnology, Oct. 2007, vol. 6(4), pp. 545-548.
Li, M. et al., "Established of an Agrobacterium-mediated cotyledon disc transformation method for Jatropha curcas," Plant Cell, Tissue and Organ Culture 2008, vol. 92, pp. 173-181.
He, Y. et al., "Agrobacterium tumefaciens-mediated Transformation of Jatropha curcas: Factors Affecting Transient Transformation Efficiency and Morphology Analysis of Transgenic Calli," Silvae Genetica, Dec. 3, 2009, vol. 58 (3), pp. 123-128.

* cited by examiner

Primary Examiner — David T Fox
Assistant Examiner — Jared Shapiro
(74) Attorney, Agent, or Firm — Rothwell, Figg, Ernst & Manbeck P.C.

(57) ABSTRACT

The present invention relates to methods for the regeneration and Agrobacterium-mediated transformation of plants in the genera of Jatropha, more specifically, in Jatropha curcas.

23 Claims, 5 Drawing Sheets

GENETIC TRANSFORMATION OF *JATROPHA CURCAS*

CROSS-REFERENCE TO RELATED APPLICATION

The present application is a continuation of U.S. patent application Ser. No. 13/139,592 filed on 14 Jun. 2011, which in turn is a national stage filing under 35 U.S.C. §371 of PCT/SG2009/000479, filed on 15 Dec. 2009, which in turn claims the benefit of priority to U.S. provisional patent application Ser. No. 61/122,454 filed 15 Dec. 2008, each application is incorporated herein by reference in its entirety.

SEQUENCE SUBMISSION

The present application is being filed along with a Sequence Listing in electronic format. The Sequence Listing is entitled 2577216SequenceListing.txt, created on 3 Apr. 2012 and is 33 kb in size. The information in the electronic format of the Sequence Listing is incorporated herein by reference in its entirety.

BACKGROUND OF THE INVENTION

The present invention relates to the field of plant regeneration and transformation, particularly to methods for the regeneration and transformation of *Jatropha*. More specifically, the present invention relates to a method and media compositions for regeneration and transformation of plants of *Jatropha curcas*.

The publications and other materials used herein to illuminate the background of the invention or provide additional details respecting the practice, are incorporated by reference, and for convenience are respectively grouped in the Bibliography.

The world is facing dwindling supply is fossil fuel and worsening Green House Effect. There is an urgent demand to increase production and consumption of renewable energy. Biofuels have been recognized as a national priority for many countries in their search for alternative sources to meet their energy security needs and at the same time help reduce $CO_2$ emissions that cause the Green House Effect. The demand for biofuel has put increasing pressure on food production. For example, to satisfy the biofuel need for Germany in 2017 as mandated by the German government the entire farm land of this country would have to be used for growing bioenergy crops with no land left for food production. To ease this competition for land and to satisfy our need for renewable fuels, there is a strong need to utilize marginal land for bio-energy production.

*Jatropha curcas* is a small woody plant belonging to the Euphorbiaceae family. Several unique characters of *Jatropha curcas* make it an ideal plant for biodiesel production. These include its rapid growth, easy propagation, low cost of seeds, high oil content, short gestation period, wide adaptability, drought tolerance and the ability to thrive on degraded soils. Moreover, its plant size renders convenient collection of seed (Jones, 1991; Sujatha et al., 2008).

However, *Jatropha* suffers from several shortcomings that may limit its wide adoption. The productivity of the plant is constrained by the unfavourable male to female flower ratio and its oil content has not been optimized by breeding. This plant is also sensitive to biotic stresses such as viral (Narayanna et al., 2007), fungal and bacterium pathogens and abiotic stresses, especially cold and drought (http colon www dot jatropha dot org). The presence of several toxic components (e.g. the protein toxin, curcin, and the cancer-causing agent phorbol esters) in seeds and leaves of the plant possess health hazards for farmers and bioprocess workers in the *Jatropha* industry.

The traditional way to improve on quality traits of plants is by breeding for superior genotypes. However, an assessment of genetic diversity using molecular markers disclosed low inter-accessional variability amongst local *J. curcas* germplasm (Sujatha at al., 2008). Therefore, alternative genetic manipulation tools, such as genetic transformation methods, are urgently required to provide additional strategies for genetic improvement of this crop. *Agrobacterium*-mediated genetic transformation has become the principal choice for generating transgenic plants. However, very few reports have appeared on the use of *Agrobacterium*-mediated transformation of plants belonging to the Euphorbiaceae family. The only one reported transformation protocol for *Jatropha* (Li et al., 2008) is not reproducible in our hands.

Thus, there is a need for methods of transforming *J. curcas* to provide means for genetic improvement in this crop species.

SUMMARY OF THE INVENTION

The present invention relates to methods for the regeneration and *Agrobacterium*-mediated transformation of plants in the genera of *Jatropha*, more specifically, in *Jatropha curcas*.

Thus, in one aspect the present invention provides an efficient and reproducible plant regeneration protocol for *J. curcas* by optimizing tissue culture and shoot regeneration conditions. This regeneration protocol has been used in combination with *Agrobacterium*-mediated transformation to produce $T_0$ transgenic *Jatropha* shoots/plants. The present invention also provides the use of a grafting step using $T_0$ transgenic shoots as scions and non-transgenic plants as root stocks. This grafting step obviates the need for regenerated plants to produce roots in tissue culture and considerably shortens the time for transgenic shoots to flower and produce $T_1$ seeds.

In one embodiment, the present invention provides a method of regenerating *J. curcas* plants. According to this embodiment, explants are obtained from cotyledons from 5-7 day old seedlings. The explants are cultured on callus formation medium which comprises MS mineral salts, B5 vitamins, citric acid, glutamine, casein hydrolysate, sucrose and 6-benzylaminopurine (6-BA) and 1-naphthaleneacetic acid (NAA) as plant hormones. Callus tissue is then transferred to a first shoot regeneration medium which comprises MS mineral salts, B5 vitamins, citric acid, glutamine, casein hydrolysate, adenine, sucrose and 6-BA and 3-indolebutyric acid (IBA) as plant hormones. Any shoots that regenerated from the callus tissue are transferred to a second shoot regeneration medium which comprises MS mineral salts, B5 vitamins, citric acid, glutamine, casein hydrolysate, sucrose and 6-BA, IBA and gibberellic acid ($GA_3$) as plant hormones. Callus tissue with no regenerates shoots are transferred to a third shoot regeneration medium which comprises MS mineral salts, B5 vitamins, citric acid, glutamine, casein hydrolysate, sucrose and 6-BA and IBA as plant hormones for further regeneration of shoots. The shoots that have regenerated are transferred to a shoot elongation medium which comprises MS mineral salts, B5 vitamins, citric acid, glutamine, casein hydrolysate, sucrose and 6-BA and $GA_3$ as plant hormones for elongation and bud multiplication. Elongated shoots are transferred to a rooting medium which comprises MS mineral salts, B5 vitamins, sucrose and IBA. After rooting, the plantlets are transferred to soil. Alternatively, the elongated shoots can be grafted to *J. curcas* root stock.

In a second embodiment, the present invention provides a method for *Agrobacterium*-mediated transformation of *J. curcas* plants. According to this embodiment, the *Agrobacterium*-mediated transformation of *J. curcas* utilizes the same basic scheme as described above for the regeneration of *J. curcas*. For transformation, the explants are first co-cultured with *Agrobacterium* cells prior to transfer to the callus formation medium with subsequent transfers to the shoot regeneration media, shoot elongation medium and rooting medium as described above. The co-culturing medium comprises MS mineral salts, B5 vitamins, citric acid, glutamine, casein hydrolysate, sucrose, glucose, acetosyringone and 6-BA and NAA as plant hormones. The callus formation medium is the same as for regeneration except that it further comprises a selective agent and an *Agrobacterium* eradicant. Similarly, the shoot regeneration media further comprise a selective agent and an *Agrobacterium* eradicant. For transformation, culturing on the callus formation medium is performed in the dark. Conventional selective agents can be used for the *Agrobacterium*-mediated transformation of *J. curcas* plants. Examples of selective agents include, but are not limited to, the herbicide BASTA, hygromycin and the like.

BRIEF DESCRIPTION OF THE FIGURES

FIG. 3A: *J. curcas* MD 5 day's seedling suitable for transformation. FIG. 3B: Callus formation and shoot generation. Left, cotyledons inoculated with *Agrobacterium* without carrying any vector. Right, cotyledons inoculated with *Agrobacterium* carrying a vector with a trait gene. Note shoot regeneration from explants. FIG. 3C: an enlarged view of hygromycin-resistant callus and shoot-like organs on the surface of brownish cotyledons. FIG. 3D: Regeneration of hygromycin-resistant shoots of *J. curcas*. FIG. 3E: Shoot elongation. FIG. 3F: Rooting of transgenic shoots. FIG. 3G: High rooting efficacy for transgenic *J. curcas*. FIG. 3H: Transgenic *J. curcas* grown on soil. FIG. 3I and FIG. 3J: Transgenic *J. curcas* shoots grafted onto non-transgenic rootstock. White arrow indicates the grafting site. FIG. 3K: Transgenic *J. crucas* flowering and seeding. The scale bars indicate 10 mm.

DETAILED DESCRIPTION OF THE INVENTION

Figure 1:
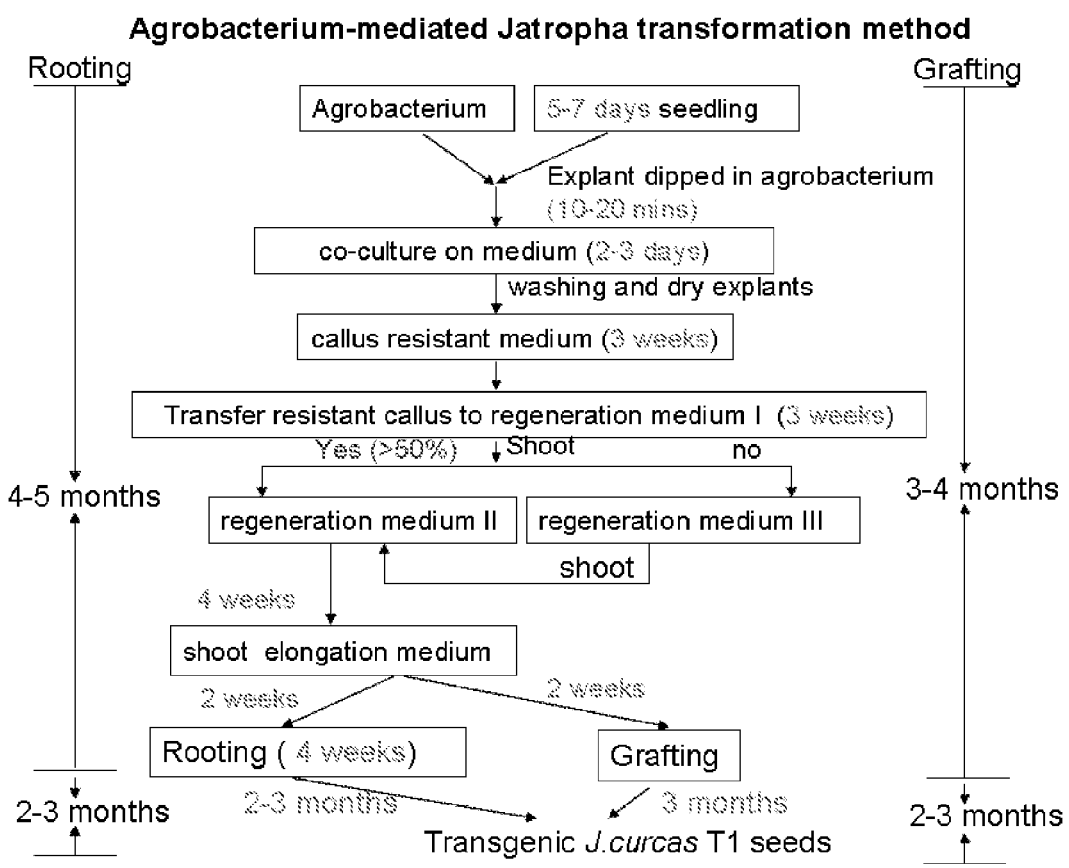
FIG. 1 illustrates an *Agrobacterium*-mediated *Jatrohpa* transformation method in accordance with the present invention. The time scale listed in the left is to use rooting protocol while the left is to use grafting protocol.

The present invention relates to methods for the regeneration and *Agrobacterium*-mediated transformation of plants in the genera of *Jatropha*, more specifically, in *Jatropha curcas*.

In one aspect, the present invention provides a method of regenerating *J. curcas* plants. According to this embodiment, explants are obtained from cotyledons from about 5 day to about 12 day old seedlings, preferably about 5-7 day old seedlings. The culturing is performed in the light at 25° C.±2° C. in a 16 h light (100 µmol/m²S)/8 h dark cycle. The seedlings are grown in tissue culture. Seed kernels of *J. curcas* are surface sterilized using conventional techniques and immersed in sterile water overnight at 28° C. in the dark. The endosperm-free embryos are germinated on hormone free germination medium with the radicals in contact with the medium. The germination medium comprises ½ strength MS mineral salts, B5 vitamins and sucrose. The concentration of sucrose is about 5% (w/v). The germination medium may further comprise a buffer. In one embodiment, the buffer is 2-(4-morpholino)ethanesulfonic acid (MES) at about 0.5 g/L at a pH of about 5.6. The germination medium is solidified with agar or phytogel. The culturing is performed in the light at 25° C.±1° C. in a 16 h light (100 µmol/m² S)/8 h dark cycle.

The explants are cultured on callus formation medium in the dark for about 2 weeks to about 3 weeks, preferably about three weeks. The callus formation medium comprises MS mineral salts, B5 vitamins, citric acid, glutamine, casein hydrolysate, sucrose and 6-benzylaminopurine (6-BA) and 1-naphthaleneacetic acid (NAA) as plant hormones. The concentration of citric acid is about 10 mg/L to about 30 mg/L, preferably about 10 mg/L. The concentration of glutamine is about 150 mg/L to about 200 mg/L, preferably about 150 mg/L. The concentration of casein hydrolysate is about 100 mg/L. The concentration of sucrose is about 3%. The concentration of 6-BA is about 1.5 mg/L. The concentration of NAA is about 0.05 mg/L. The callus formation medium preferably further comprises $MgCl_2$ at a concentration of about 0.5 g/L to about 0.95 g/L, preferably 0.5 g/L. The callus formation medium has a pH of about 5.8 to about 6.0. The callus formation medium is solidified with agar or phytagel, preferably phytagel at a concentration of about 2.5 g/L to about 3 g/L, preferably 2.5 g/L.

Callus tissue is then transferred to a first shoot regeneration medium and cultured in the light for about 2 weeks to about 3 weeks, preferably about three weeks. The first shoot regeneration medium comprises MS mineral salts, B5 vitamins, citric acid, glutamine, casein hydrolysate, adenine, sucrose and 6-BA and 3-indolebutyric acid (IBA) as plant hormones. The concentrations of the citric acid, glutamine, casein hydrolysate and 6-BA are the same as in the callus formation medium. The concentration of adenine is about 2 mg/L to about 4 mg/L, preferably about 2 mg/L. The concentration of IBA is about 0.05 mg/L. The first shoot regeneration medium preferably further comprises $MgCl_2$ at a concentration of about 0.5 g/L to about 0.95 g/L, preferably 0.5 g/L. The first shoot regeneration medium has a pH of about 5.8 to about 6.0. The first shoot regeneration medium is solidified with agar or phytagel, preferably phytagel at a concentration of about 2.5 g/L to about 3.0 g/L, preferably 2.5 g/L.

Any shoots that regenerated from the callus tissue are transferred to a second shoot regeneration medium and cultured in the light for about 3 weeks to about 4 weeks, preferably about four weeks. The second shoot regeneration medium comprises MS mineral salts, B5 vitamins, citric acid, glutamine, casein hydrolysate, sucrose and 6-BA, IBA and gibberellic acid ($GA_3$) as plant hormones. The concentrations of the citric acid, glutamine, casein hydrolysate, 6-BA and IBA are the same as in the first shoot regeneration medium. The concentration of $GA_3$ is about 0.05 mg/L to about 0.5 mg/L, preferably about 0.5 mg/L. The second shoot regeneration medium preferably further comprises $MgCl_2$ at a concentration of about 0.5 g/L. The second shoot regeneration medium has a pH of about 5.8 to about 6.0. The second shoot regeneration medium is solidified with agar or phytagel, preferably agar at a concentration of about 6.5 g/L to about 7 g/L, preferably 7 g/L.

Callus tissue with no regenerates shoots are transferred to a third shoot regeneration medium and cultured in the light for about 4 weeks to about 5 weeks, preferably about 4 weeks. The third shoot regeneration medium comprises MS mineral salts, B5 vitamins, citric acid, glutamine, casein hydrolysate, sucrose and 6-BA and IBA as plant hormones for further regeneration of shoots. The concentration of the citric acid, glutamine, casein hydrolysate, 6-BA and IBA are the same as in the first shoot regeneration medium. The third shoot regeneration medium preferably further comprises $MgCl_2$ at a concentration of about 0.5 g/L to about 0.95 g/L, preferably 0.5 g/L. The third shoot regeneration medium has a pH of about 5.8 to about 6.0. The third shoot regeneration medium is solidified with agar or phytagel, preferably phytagel at a concentration of about 2.5 g/L to about 3 g/L, preferably 2.5 g/L.

The shoots that have regenerated on the second shoot regeneration medium are transferred to a shoot elongation medium and cultured in the light for about 2 weeks to about 3 weeks, preferably about two weeks. The shoot elongation medium comprises MS mineral salts, B5 vitamins, citric acid, glutamine, casein hydrolysate, sucrose and 6-BA and $GA_3$ as plant hormones for elongation and bud multiplication. The concentrations of the citric acid, glutamine and casein hydrolysate are the same as in the first shoot regeneration medium. The concentration of 6-BA is about 0.3 mg/L. The concentration of $GA_3$ is about 0.1 mg/L to about 0.5 mg/L, preferably about 0.1 mg/L. The shoot elongation medium has a pH of about 5.8 to about 6.0. The shoot elongation medium is solidified with agar or phytagel, preferably agar at a concentration of about 6.5 g/L to about 7 g/L, preferably 7 g/L.

Elongated shoots are transferred to a rooting medium and cultured in the light for about 3 weeks to about 4 weeks, preferably about four weeks. The rooting medium comprises MS mineral salts, B5 vitamins, sucrose and IBA. The concentration of sucrose is about 3%. The concentration of IBA is about 0.07 mg/L. The rooting medium has a pH of about 5.6. The rooting medium is solidified with agar or phytagel, preferably phytagel at a concentration of about 2.2 g/L. After rooting, the plantlets are transferred to soil. Alternatively, the elongated shoots can be grafted to *J. curcas* root stock using conventional techniques instead of being transferred to the rooting medium.

In a second aspect, the present invention provides a method for *Agrobacterium*-mediated transformation of *J. curcas* plants. According to this embodiment, the *Agrobacterium*-mediated transformation of *J. curcas* utilizes the same basic scheme as described above for the regeneration of *J. curcas*. Vectors containing DNA of interest are introduced into *Agrobacterium* using conventional techniques, such as electroporation. Transformed *Agrobacterium* cells are cultured prior to use using conventional techniques. In accordance with one such technique, *Agrobacterium* cells are inoculated into LB medium supplemented with kanamycin and carbicillin. The concentration of kanamycin is about 25 mg/L to about 100 mg/L, preferably about 50 mg/L. The concentration of carbicillin is about 50 mg/L to about 100 mg/L, preferably about 100 mg/L. The *Agrobacterium* cells are grown overnight at 28° C., 250 rpm. The *Agrobacterium* cells are collected by centrifugation and re-suspended in liquid MS medium supplemented with sucrose, glucose, acetosyringone (AS), 6-BA and NAA. The concentration of sucrose is about 30 g/L. The concentration of glucose is about 10 g/L. The concentration of AS is about 20 mg/L. The concentration of 6-BA is about 1.5 mg/L. The concentration of NAA is about 0.05 mg/L to about 0.1 mg/L, preferably about 0.1 mg/L.

For transformation, the explants are first co-cultured with *Agrobacterium* cells prior to transfer to the callus formation medium with subsequent transfers to the shoot regeneration media, shoot elongation medium and rooting medium as described above. The co-culturing is performed in the dark for about 2-3 days. The co-culturing medium comprises MS mineral salts, B5 vitamins, citric acid, glutamine, casein hydrolysate, sucrose, AS and 6-BA and NAA as plant hormones. The concentrations of citric acid, glutamine, casein hydrolysate and sucrose are the same as in the callus formation medium. The concentration of AS is about 20 mg/L. The concentration of 6-BA is about 1.5 mg/L. The concentration of NAA is about 0.05 mg/L to about 0.1 mg/L, preferably about 0.05 mg/L. The co-culturing medium may further comprise a suitable buffer. In one embodiment, the buffer is MES. The concentration of MES is about 0.5 g/L at a pH of about 5.0 to about 5.2.

The callus formation medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 3 mg/L to about 5 mg/L, preferably 3.5 mg/L. In another embodiment, the selective agent is glufosinate ammonium at a concentration of about 1 mg/L. The *Agrobacterium* eradicant may be any conventional eradicant, such as cefotaxinme, and the like. In one embodiment, the *Agrobacterium* eradicant is cefotaxinme at a concentration of about 100 mg/L to about 150 mg/L, preferably 100 mg/L. Culturing on the callus formation medium for *Agrobacterium*-mediated transformation is performed in the dark for about 2 weeks to about 3 weeks, preferably about 3 weeks.

The callus tissue is then treated as described above with respect to the regeneration of *J. curcas* with transfers and culturing in the light as described above to the first shoot regeneration medium, second shoot regeneration medium, third shoot regeneration medium, shoot elongation medium, rooting medium or grafting. The first shoot regeneration medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 3 mg/L to about 5 mg/L, preferably 3.5 mg/L. In another embodiment, the selective agent is glufosinate ammonium at a concentration of about 1 mg/L. The *Agrobac-*

*terium* eradicant may be any conventional eradicant, such as cefotaxinme In one embodiment, the *Agrobacterium* eradicant is cefotaxinme at a concentration of about 100 mg/L to about 150 mg/L, preferably 100 mg/L.

The second shoot regeneration medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 4 mg/L to about 5 mg/L, preferably 4 mg/L. In another embodiment, the selective agent is glufosinate ammonium at a concentration of about 1 mg/L. The *Agrobacterium* eradicant may be any conventional eradicant, such as cefotaxinme. In one embodiment, the *Agrobacterium* eradicant is cefotaxinme at a concentration of about 100 mg/L to about 150 mg/L, preferably 100 mg/L.

The third shoot regeneration medium used for the *Agrobacterium*-mediated transformation of *J. curcas* is the same as that used for regeneration except that it further comprises a selective agent and an *Agrobacterium* eradicant. The selective agent may be any selective agent for which a marker gene, such as described below, has been included in the transformed *Agrobacterium*. In one embodiment, the selective agent is hygromycin at a concentration of about 3 mg/L to about 5 mg/L, preferably 3.5 mg/L. In another embodiment, the selective agent is glufosinate ammonium at a concentration of about 1 mg/L. The *Agrobacterium* eradicant may be any conventional eradicant, such as cefotaxinme. In one embodiment, the *Agrobacterium* eradicant is cefotaxinme at a concentration of about 100 mg/L to about 150 mg/L, preferably 100 mg/L.

The shoot elongation medium and the rooting medium used for the *Agrobacterium*-mediated transformation of *J. curcas* are the same as that used for regeneration.

The DNA that is inserted (the DNA of interest) into plants of the genera *Jatropha* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Plant Materials and Culture Methods:
*Jatropha curcas* (L.) MD seeds were obtained from Indonesia. After removing the outer seed coat, seeds kernel were surface sterilized for 60 seconds with 75% (v/v) ethanol, following immersed in 10% (v/v) $H_2O_2$ for 1 h, then rinsed with sterile water for two times, finally immersed in sterile water overnight at 28° C. in darkness. The endosperm-free embryos were germinated on hormone-free half-strength Murashige and Skoog salt (½ MS) medium (Murashige and Skoog, 1962) containing B5 Vitamins (Gamborg et al., 1968), 5 g/L sucrose, 0.5 g/L 2-(4-morpholino)ethanesulfonic acid (MES) and 2.2 g/L phytagel (Sigma), pH 5.6, with the radicals in contact with the medium, and cultured in a tissue culture room, at 25° C.±2° C. in a 16h light (100 µmol/$m^2$ S)/8 h dark cycle.
Media:
The media used in the present invention are as follows.

Medium I (Basal Medium):
MS major salts, MS minor salts and B5 vitamins, 10 mg/L citric acid, 150 mg/L glutamine, 100 mg/L casein enzymatic hydrolysate, 3% (w/v) sucrose, 0.5 g/L $MgCl_2$ (only used in phytagel-containing medium) in combination with plant growth regulators was used. Medium I was adjusted to pH 5.8-6.0 with 1 N KOH, solidified with 2.5 g/L phytagel and autoclaved at 121° C. for 20 min. All plant growth regulators were filter sterilized before being added to autoclaved medium.
Co-Cultivation Medium:
basal medium plus 20 mg/L acetosyringone (AS), 0.5 g/L MES, 1.5 mg/L 6-benzylaminopurine (6-BA) and 0.05 mg/L 1-naphthaleneacetic acid (NAA), pH 5.0-5.2.
Callus Formation Medium:
basal medium plus 1.5 mg/L 6-BA, 0.05 mg/L NAA, 3.5 mg/L hygromycin (hyg, A.G scientific, San Diego, Calif.) as selective agent for plant transformation or 1 mg/L glufosinate ammonium (BASTA, Crescent Chemical, NY) and 100 mg/L cefotaxinme (Cef) for elimination of *Agrobacteria* cells.
Shoot Regeneration Medium I:
basal medium plus 1.5 mg/L 6-BA, 0.05 mg/L 3-indolebutyric acid (IBA), 2 mg/L adenine (adenine hemisulfate salt, SIGMA), 3.5 mg/L Hyg or 1 mg/L glufosinate ammonium and Cef 100 mg/L.
Shoot Regeneration Medium II:
basal medium plus 1.5 mg/L 6-BA, 0.05 mg/L IBA, 0.5 mg/L gibberellic acid ($GA_3$), 4 mg/L Hyg or 1 mg/L glufosinate ammonium and 100 mg/L Cef 100, change phytagel to 7 g/L agar.
Shoot Regeneration Medium III:
basal medium plus 1.5 mg/L 6-BA, 0.05 mg/L IBA, 3.5 mg/L Hyg or 1 mg/L glufosinate ammonium and 100 mg/L Cef.
Shoot Elongation Medium:
basal medium plus 0.3 mg/L 6-BA, 0.1 mg/L $GA_3$, change phytagel to 7 g/L agar.
Rooting Medium:
MS major salts, MS minor salts and B5 vitamins, 3% sucrose, 0.5 g/L MES, 0.07 mg/L IBA, 2.2 g/L phytagel, pH5.6.
Medium II: liquid MS medium supplemented with 10 g/L glucose, 0.5 g/L MES, 20 mg/L AS, 1.5 mg/L 6-BA, 0.1 mg/L NAA, pH 5.0-5.2.
RNA Extraction and Analysis:
Fresh leaf or seed tissue (100 mg) was ground in liquid nitrogen and extracted with plant RNA purification reagent (Invitrogen). RNA concentration was measured by Nanodrop (Thermo, USA). DNase treatment and reverse transcription (RT) reaction were performed as described (Qu et al., 2007).
*Agrobacterium* Strain and Vectors:
*J. curcas* WRINKLE1 (JcWRI1) and DGAT1 sequences were identified by sequencing a *Jatropha* seed cDNA library. The JcWRI1 full-length cDNA was amplified from *J. curcas* seed first stranded cDNA product with two primers 5'-AATC GGATCCTAATGAAGAGGTCTTCTGCT-3' (SEQ ID NO:1) and 5'-TCATG TTAATTAATCAAACAGAATAGTTACAAGAAA-3' (SEQ ID NO:2) (underlined nts are enzyme recognition sites). The PCR product was further inserted into the pBA002-MYC vector treated with the BamHI and PacI to form pBA002-MYC-JcWRI1. The JcDGAT1 full-length cDNA was amplified from *J. curcas* seed first stranded cDNA product with two primers 5'-CAATA TCTAGACCATGACGATTTTGGAGACCACT-3' (SEQ ID NO:3) and 5'-TATT AGATCTGGTCTTAATTCAGCATTGCC-3' (SEQ ID NO:4) (underlined nts are enzyme recognition sites). The PCR product was further inserted into the pBA002-HA vector treated with XbaI and BamHI to form pBA002-JcDGAT1-HA. The RcFAH12 full-length cDNA was amplified from castor bean seed first stranded cDNA product with two primers: 5'-CAATATCTAGACCATGGGAGGTGGTGGTC-3' (SEQ ID NO:5) and 5'-TGTAGGATCCGGATACTTGTTCCGGTACCAG-3' (SEQ ID NO:6) (underlined nts are enzyme recognition sites). The PCR product was further inserted into the pBA002-HA vector treated with XbaI and BamHI to form pBA002-RcFAH12-HA. Vectors were introduced into *Agrobacterium* strain AGL1 by electroporation (BIO-RAD, CA, USA). Transformed *Agrobacterium* cells were used to inoculate liquid LB medium supplemented with 50 mg/L kanamycin (for pCAMBIA 1300-GFP) or 50 mg/L spectimycin (for pBA002-MYC-WRI1, pBA002-JcDGAT1-HA, pBA002-RcFAH12-HA) and 100 mg/L carbicillin and were grown overnight at 28° C., 250 rpm to a final $OD_{595}$ 0.7-1. *Agrobacterium* cells were collected by centrifugation at 4200 rpm for 10 min at 20° C. The cell pellet was re-suspended with Medium II and adjusted to an $OD_{595}$ of 0.25-0.35 (only *Agrobacterium* AGL1) prior to co-cultivation.

Isolation of DNA from *J. curcas* Leaves and Genotype Analysis:

Fifty mg of fresh *J. curcas* leaves were disrupted in liquid nitrogen and incubated at 65° C. for one hour after addition of 400 µL CTAB extraction buffer (100 mM Tris, pH 8.0; 1.4 M NaCl; 20 mM EDTA; 2% cetyl trimethylammonium bromide (CTAB)). After two times extraction with chilled-chloroform, DNA was precipitated with isoprepanol and collected by centrifugation. For hygromycin gene genotyping, the primers used were hyg5: 5'-CGATGTAGGAGGGCGTGG-3' (SEQ ID NO:7), hyg3: 5'-ACTTCTACACAGCCATCGGT CC-3' (SEQ ID NO:8). For bar gene genotyping, the primers used were bar5: 5'-GTCTGCAC CATCGTCAACC-3' (SEQ ID NO:9), bar3: 5'-GAAGTCCAGCTGCCAGAAAC-3' (SEQ ID NO:10).

Antibodies and Protein Gel Blot Analysis:

Curcin protein antibody was prepared by Dr. Yin Zhongcao's lab. Western blot analysis was performed as previously described (Qu et al., 2007). Total plant proteins were separated by 12% sodium dodecyl sulfate-polyacrylamide gel electrophoresis. ECL peroxidase conjugated donkey anti-rabbit immunoglobulin G was used as a secondary antibody Immunoreactive bands were visualized using ECL Western blotting Detection Reagents (GE healthcare).

Example 2

*J. curcas* Cotyledon Explant Transformation

Figure 2:
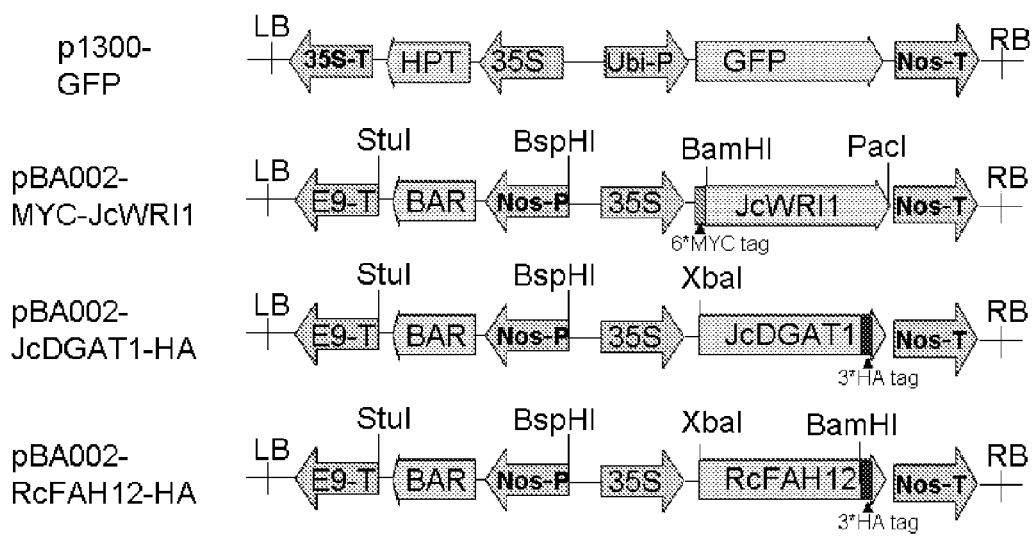
FIG. 2 illustrates *Agrobacterium* transformation vectors utilized to demonstrate the transformation method of the present invention.

FIG. 1 illustrates the *Agrobacterium*-mediated *Jatropha* transformation method as set forth in further detail in this Example. FIG. 2 illustrates the *Agrobacterium* transformation vectors that were used in this Example.

Figure 3:
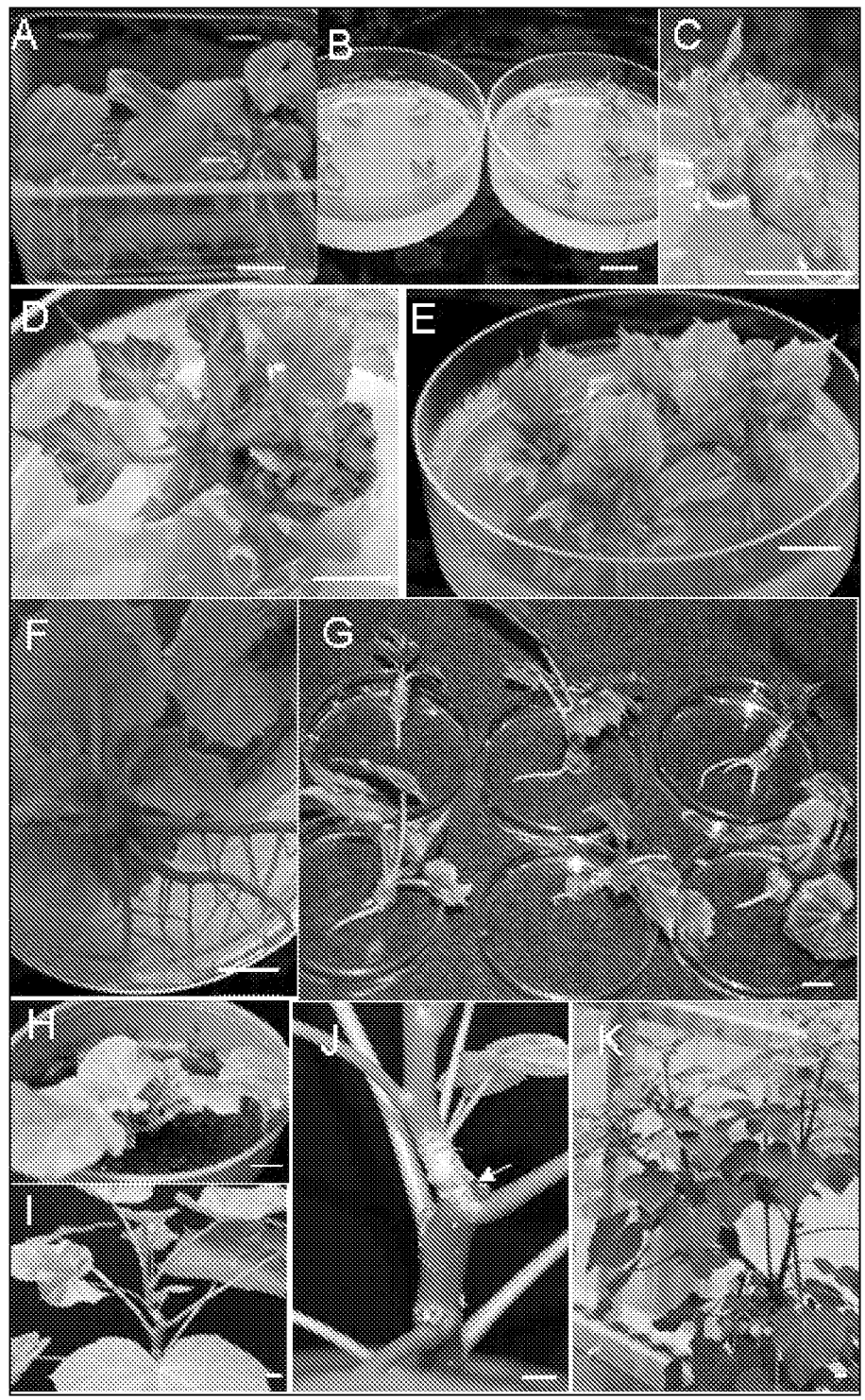
FIGS. 3A-3K show the transformation, regeneration, flowering and seedling of *J. curcas*.

Co-Cultivation:

Cotyledons from 5-7 day old seedlings (Example 1; FIG. 3A) were cut into small pieces (5×5 mm) and incubated with *Agrobacterium* cells (Example 1) harboring the target expression cassette in 20 ml of medium II for 10-20 min at 25° C. Explants were then transferred to the co-cultivation medium for 2-3 days at 22° C. in the dark. Following co-cultivation, explants were rinsed several times with sterile water, following one wash with 300 mg/L cefotaxine. Cotyledon tissues were blotted dry by putting them on a pad of sterilized paper to remove excess surface water.

Selection of hygromycin-resistant or glufosinate ammonium-resistant calli: After co-cultivation, the explants were plated onto the callus formation medium plate and transferred to darkness at 25° C.±1° C. for three weeks. The nontransformed and transformed explants form callus tissue (FIG. 3B) and some form callus upon culturing (FIG. 3B, right panel; FIG. 3C). Nontransformed explants normally will turn brown when cultured in the dark.

Shoot Regeneration:

Explants with newly emerged hygromycin-resistant or glufosinate ammonium-resistant callus were transferred onto the shoot regeneration medium I for 3 weeks at 25° C. with 16 h light (100 µmol/m² $S^1$)/8 h dark cycles. The methods described here are based on direct shoot induction from transformed callus by adding adenine. While the term "regeneration" is used here to describe the re-creation of a whole plant from such transformed calli. Although 6-BA (6-benzyladenine) has similar effect on shoot regeneration, it can not be used in this special step during the methods described here. Furthermore, higher or lower concentration, early adding or later adding adenine will make the shoot regeneration more difficult or unnormal shooting. In an alternative embodiment, the method for obtaining shoot regeneration involves adding 2 mg/L plus normal 6-BA or other adenine derivative such as 2-isopentenyl adenine. During this period, any shoots regenerated from calli (about 40-50%) were transferred to the shoot regeneration medium II (FIG. 3D). Calli with no regenerated shoots were transferred to the shoot regeneration medium III for further culturing and regeneration of shoots.

Shoot Elongation:

After 4 weeks, regenerated shoots were transferred onto shoot elongation medium for elongation and bud multiplication (FIG. 3E).

Rooting:

The elongated shoots about 2.5 cm in length were rooted in rooting medium (FIG. 3F). Normally it takes more than one month to get roots such as shown in FIG. 3F. Our rooting protocol can provide high rooting efficacy about 45% (FIG. 3G) and one main root length longer than 10 mm can be successfully transferred into soil and get more than 90% live (FIG. 3H).

Grafting:

Elongated, transgenic shoots can also be used as scions for grafting onto non-transgenic root stocks. Healthy and vigorously growing *J. curcas* plants were chosen to be rootstocks. Both scions and rootstocks were cut into the cambium region so that phloem tissues from both will connect after joining The graft joint was wrapped with parafilm and secured by a tape. Grafted *J. curcas* plants were maintained under low light intensity (28° C. with 16 h light (50 µmol/m² $S^1$)/8 h dark cycles) and 85% humidity for 7 days. Transgenic *J. curcas* shoots grafted onto non-transgenic root stock are shown in FIGS. 3I and 3J. Transgenic *J. curcas* plant showed normal flowering and seeding in greenhouse (FIG. 3K).

Example 3

Transformation and Analysis of Transgenic *J. curcas*

Examples of *Jatropha* transformation and regeneration of BASTA or hygmycin plants from the transformed cells using the method of the present invention are detailed below. Briefly, the method requires that a heterologous DNA construct comprising a plant promoter, a DNA sequence encoding a protein that confers a selective advantage, such as BASTA or hygromycin tolerance, and a 3' untranslated transcriptional terminator region be provided. The DNA constructs comprise a plant promoter operably connected to a DNA coding region encoding a protein that confers BASTA or hygromycin tolerance, and a 3' termination signal. Preferably, the DNA construct encodes an additional gene of interest. For example, the DNA construct may include a gene the expression of which results in increased yields or altered fatty acid content in transformed plants.

In the example below, hygromycin tolerant *Jatropha* plants expressing green fluorescent protein (GFP) were obtained from tissue that was transformed with DNA constructs that included a GFP gene. This GFP gene and other genes such as GUS, luciferase gene, which can serve as easily screenable markers, were used in some of the examples described below, simply because their phenotypes can be readily detected in the transformed plants. It is reasonable to expect that by using DNA constructs created by standard molecular biological techniques, the present invention may be employed to obtain a *Jatropha* plants expressing virtually any other gene. In an alternative embodiment, the method for obtaining transformed *Jatropha* plants involves the cotransformation of two DNA constructs, one of which comprises a selectable marker, such as a BASTA or hygromycin tolerance marker, and the other of which comprises a gene of interest.

Figure 4:
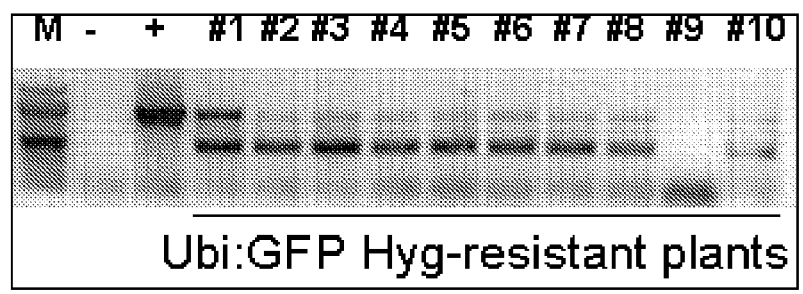
FIG. 4 shows PCR analyse of hyg-resistant ubi:GFP *J. curcas* plants. Lane −: wildtype *Jatropha* control; Lane +: plasmid DNA of p1300-GFP; Lanes #1-#10 from hygromycin-resistant *Jatropha* shoot leaves.
Figure 5:
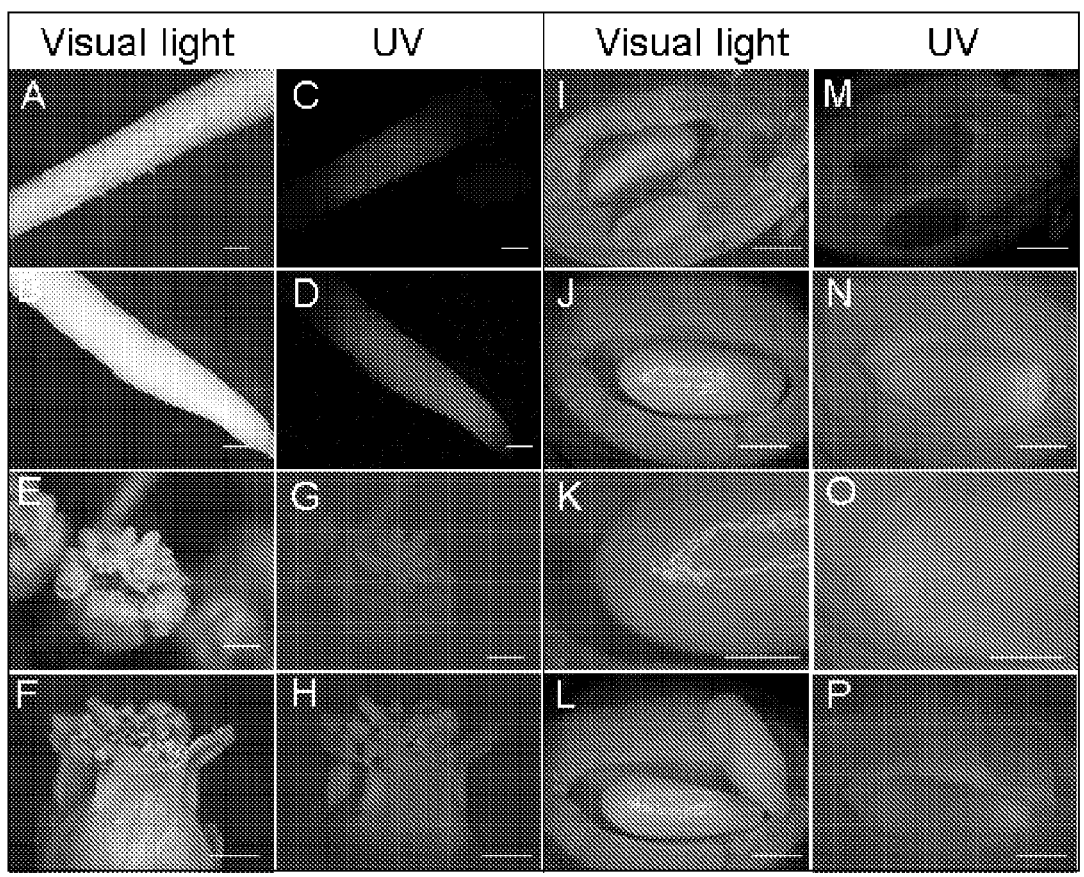
FIGS. 5A-5P show the expression of GFP in $T_0$ plant root (FIG. 5B, FIG. 5D), male flower (FIG. 5F, FIG. 5H), and $T_1$ seeds 3 week after fertilization (FIG. J, FIG. K, FIG. L, FIG. N, FIG. O, FIG. P). FIG. A, FIG. C, FIG. E, FIG. G, FIG. I and FIG. M are wildtype controls for every plant organ. The scale bars indicate 2 mm.

The transformation and shoot regeneration of hygromycin resistant putative GFP transgenic *Jatropha* plants was accomplished according to the method described in Example 2. Genomic DNA of hygromycin resistant shoots was extracted with the method described in Example 1. Genotyping was performed with the hygromycin gene primer pair (SEQ ID N0:7 and SEQ ID N0:8). Nine of 10 events were PCR positive, while the non-transformation control shows no band in the CK lane (FIG. 4). GFP expression was fast screened when transgenic *Jatropha* roots were excited with ultraviolet light (FIG. 3B). The fluorescence indicated that this new introduced GFP expression cassette was expressed in $T_0$ *Jatropha* plants. After ubi:GFP transgenic *Jatropha* flowering, we checked the GFP expression in the inflorescence. The male flower, especially the pollen has some weak green fluoresce (FIG. 5H). We also checked GFP expression in the 3 week after fertilization seeds. Strong GFP expression can be seen in the whole transgenic $T_1$ seed both from outside (FIG. 5N, FIG. 5O) or inside (FIG. 5P). This indicates GFP also express well in the progeny seeds in transgenic *Jatropha*.

Triacylglycerols (TAG) is the main energy storage form after the plant converts solar energy into chemical energy. But the standard biochemical route for its synthesis was thought to be quite wasteful when plants use a variation of glycolysis as an intermediate. WRINKLED1 (WRI1), a transcription factor of the AP2/EREB family, has an impact on more specific aspects of the seed storage process especially transcriptional control conversion of sugar variants into TAG, and therefore, shows a very important role in control seed oil content. Expression of the *Arabidopsis* WRI1 cDNA under the control of the cauliflower mosaic virus 35S-promoter led to increased 10-20% seed oil content. Moreover, the ectopic expression of the WRINKLED1 cDNA caused the accumulation of triacylglycerols in developing seedlings (Cernac and Benning, 2004). We proposed that ectopic expression of *Jatropha* WRI1 gene in *Jatropha* would lead to higher oil content. In addition, the transgenic seedling can develop into embryos or embryo-like organ producing oil when fed with sugars, just like a lipid reactor that can be supplied with sugar-containing liquid substrate for the constitutive CaMV 35S promoter-driven to WRI1 strong expression in vegetative organs.

Figure 6:
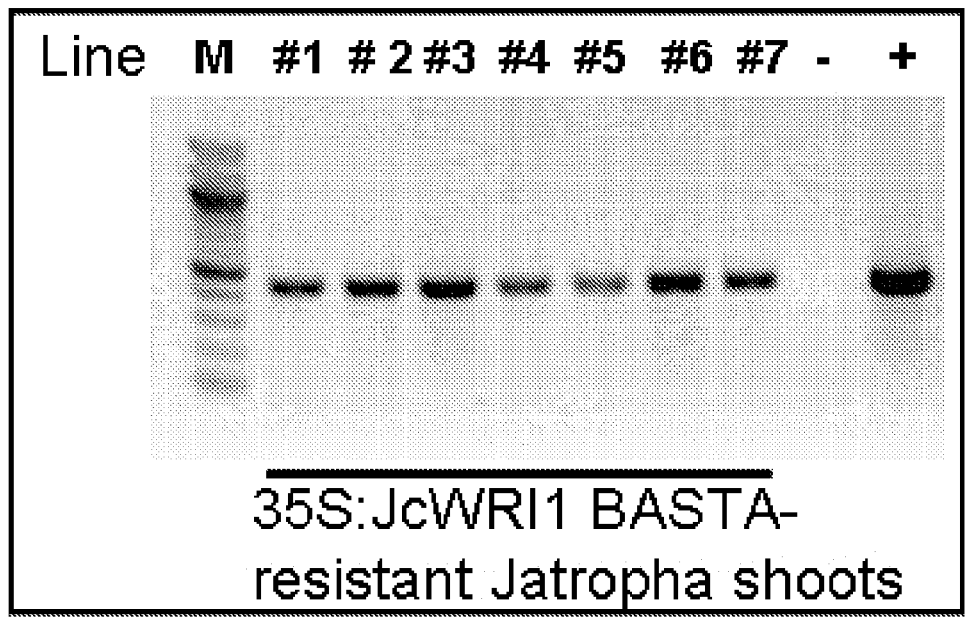
FIG. 6 shows PCR analyses of BASTA-resistant 35S: JcWRI1 *J. curcas* plants. Lane M, DNA ladder; Lane #1-#7 from BASTA-resistant *Jatropha* shoot leaves; lane −, wildtype control; lane +, plasmid DNA of pBA002-MYC-JcWRI1.

We cloned the full-length cDNA of *Jatropha* WRI1 (JcWRI1) PCR amplified from *Jatropha* seed RT-PCR products using PCR primers (SEQ ID NO:1 and SEQ ID NO:2) for the JcWRI1 clone sequence derived from the *Jatropha* seeds cDNA library sequencing. The full length JcWRI1 cDNA sequence is set forth in SEQ ID NO:11. The overexpression vector (pBA002-MYC-JcWRI1) having the JcWRI1 cDNA under the control of CaMV 35S promoter was constructed and transformed into the *Agrobacterium* AGL1 strain. The proposed 6xMYC tag fusion WRI1 could be detected with MYC tag antibody. Transformation and shoot regeneration of BASTA resistant putative JcWRI1 overexpression transgenic *Jatropha* plants was accomplished according to the method described in Example 2. Genomic DNA of hygmycin resistant shoots was extracted with the method described in Example 1. Genotyping was performed with the BASTA gene primer pair (SEQ ID NO:9 and SEQ ID NO:10). All events we tested were PCR positive, while the non-transformation control showed no band in the CK (FIG. 6).

Plant and animal diacylglycerol acyltransferases (DGAT) are responsible for packaging of nascent fatty acids into TAGs, which subsequently accumulate in oil bodies that bud off from the endoplasmic reticulum. Plant type 1 DGAT (DGAT1) genes have been shown to contribute significantly to seed oil content, both by overexpression and through mutational downregulation studies (Zou et al., 2999; Jako et al., 2001). We proposed that ectopic expression of *Jatropha* DGAT1 gene in *Jatropha* would leads to higher level oil content.

Figure 7:
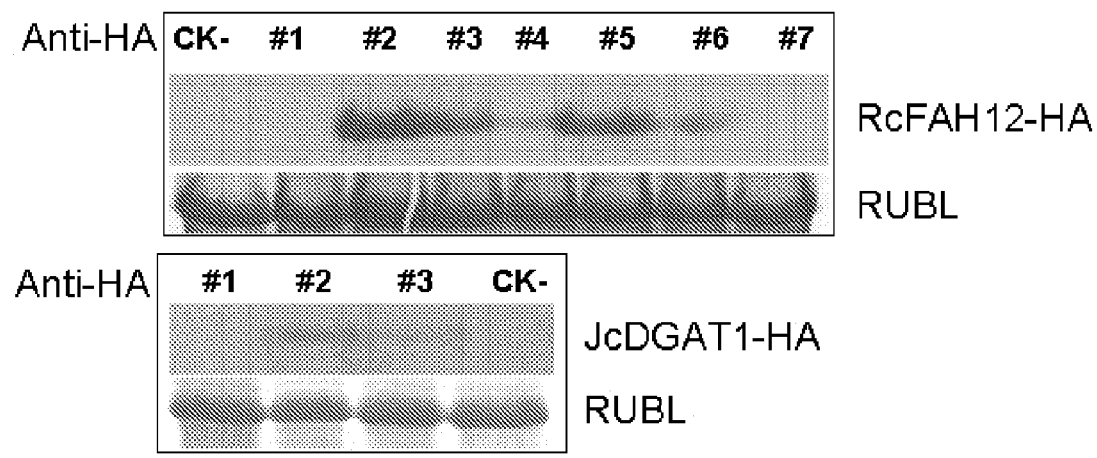
FIG. 7 shows Western blot analysis of RcFAH12 and JcDGAT1 levels in leaves of transgenic *Jatropha* plants expressing 35S:RcFAH12 and 35S:JcDGAT1 using anti-HA antibody. Bottom panel: Coomassie Bright Blue staining of the RUBL (the large subunit of RUBISCO) which serves as a loading control.

We cloned the full-length *Jatropha* DGAT1 cDNA from *Jatropha* seed RT-PCR products using PCR primers (SEQ ID NO:3 and SEQ ID NO:4) according to the DGAT1 clone sequence. The full length JcDGAT1 cDNA sequence is set forth in SEQ ID NO:13. The overexpression vector (pBA002-JcDGAT1-HA) having the JcDGAT1 cDNA under the control of CaMV 35S promoter was constructed and transformed into the *Agrobacterium* AGL1 strain. The proposed 3xHA tag fusion DGAT1 could be detected with HA tag antibody. Transformation and shoot regeneration of BASTA resistant putative JcDGAT1 transgenic *Jatropha* plants was accomplished according to the method described in Example 2. 35S-JcDGAT1 expression was proved by Western blot based on HA-antibody with the method describing in Example 1 (FIG. 7). HA-specific band can be seen in two lanes out of three transgenic *Jatropha* lines.

Plant oils (and their derivatives) can be used in numerous cases and applications for plant-derived industrial feedstocks. When compared with non-renewable petroleum, the renewable nature making them especially attractive for many industrial applications for total loss applications where environmental concerns are an issue. Castor (*Ricinus communis*) oil has numerous applications in transportation, cosmetics and pharmaceuticals, and manufacturing industries. Castor oil contains more than 90% ricinoleic acid, which is a monounsaturated, 18-carbon fatty acid. It is unusual in that it has a hydroxyl functional group on the twelfth carbon. This functional group causes ricinoleic acid (and castor oil) to be unusually polar (http colon en dot wikipedia dot org slash wiki slash Castor_oil). One specific enzyme: fatty acid hydroxylase 12 (FAH12) is responsible for adding the hydroxyl group instead of normal FAD2 function to introduce unsaturated band on the twelfth carbon (van de Loo et al., 1995). Compared to other seed oils which lack the hydroxyl group, castor oil demands a higher price. Despite a widespread demand for castor oil, however, cultivation of this crop is restricted due to the presence of a toxin (ricin) and allergenic proteins, and thus the cost of castor oil is relatively high. Transgenic exogenous FAH12 can produce hydroxyl-castor oil in *Arabidopsis* seeds (Lu et al., 2006). We proposed that ectopic expression of castor bean FAH12 gene in *Jatropha* would lead to the production of castor oil.

We cloned the full-length castor bean FAH12 cDNA (RcFAH12) from castor bean seed RT-PCR products using PCR primers (SEQ ID NO:5 and SEQ ID NO:6) according to the FAH12 CDS sequence. The full length RcFAH12 cDNA sequence is set forth in SEQ ID NO:15. The overexpression vector (pBA002-RcFAH12-HA) having the RcFAH12 cDNA under the control of CaMV 35S promoter was constructed and transformed into the *Agrobacterium* AGL1 strain. The proposed 3xHA tag fusion RcFAH12 could be detected with HA tag antibody. Transformation and shoot regeneration of BASTA resistant putative RcFAH12 transgenic *Jatropha* plants was accomplished according to the method described in Example 2. 35S-RcFAH12 expression was proved by Western blot based on HA-antibody with the method describing in Example 1. HA-specific band can be seen in 5 lanes out of 7 transgenic *Jatropha* lines (FIG. 7). Two lines, #2 and #5, have very high FAH12-HA fusion expression protein level.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Cernac, A. and Benning, C. (2004). WRINKLED1 encodes an AP2/EREB domain protein involved in the control of storage compound biosynthesis in *Arabidopsis*. *Plant J* 40:575-585.

Gamborg, O. L. et al. (1968). Nutrient requirements of suspension cultures of soybean root cells. *Exp Cell Res* 50:151-158.

Jako, C. et al. (2001). Seed-specific over-expression of an *Arabidopsis* cDNA encoding a diacylglycerol acyltransferase enhances seed oil content and seed weight. *Plant Physiol* 126:861-874.

Jones, N. M. J. (1991). *Jatropha curcas*—a multipurpose species for problematic sites. *Land Resources Series* 1:1-12.

Li, M. L. H. et al. (2008). Establishment of an *Agrobacterium*-mediated cotyledon disc transformation method for *Jatropha curcas*. *Plant Cell Tiss Org Cult* 92:173-181.

Lu, C. et al. (2006). A high-throughput screen for genes from castor that boost hydroxy fatty acid accumulation in seed oils of transgenic *Arabidopsis*. *Plant J* 45:847-856.

Murashige, T. and Skoog, F. (1962). A revised medium for rapid growth and bioassays with tobacco tissue cultures. *Physiol Plant* 15:473-497.

Narayana, D. S. A et al. (2007). Distinct Begomoviruses Closely Related to Cassava Mosaic Viruses cause Indian *Jatropha* Mosaic Disease. *Int'l J Virol* 3:1-11.

Qu, J. et al. (2007). Artificial microRNA-mediated virus resistance in plants. *J Virol* 81:6690-6699.

Sujatha, M. et al. (2008). Role of biotechnological interventions in the improvement of castor (*Ricinus communis* L.) and *Jatropha curcas* L. *Biotechnol Adv* 26:424-435.

van de Loo, F. J. et al. (1995). An oleate 12-hydroxylase from *Ricinus communis* L. is a fatty acyl desaturase homolog. *Proc Natl Acad Sci USA* 92:6743-6747.

Zou, J. et al. (1999). The *Arabidopsis thaliana* TAG1 mutant has a mutation in a diacylglycerol acyltransferase gene. *Plant J* 19:645-653.

What is claimed is:

1. An isolated nucleic acid comprising the nucleotide sequence set forth in SEQ ID NO: 11.

2. A nucleic acid molecule comprising a heterologous plant operable promoter operably linked to a nucleic acid encoding a protein comprising the amino acid sequence set forth in SEQ ID NO:12.

3. The isolated nucleic acid of claim 1 which further comprises a plant operable promoter operably linked to the nucleic acid.

4. The nucleic acid molecule of claim 2, wherein the plant operable promoter is a constitutive promoter, an inducible promoter or a tissue-preferred promoter.

5. The isolated nucleic acid of claim 3, wherein the plant operable promoter is a constitutive promoter, an inducible promoter or a tissue-preferred promoter.

6. An expression vector comprising the isolated nucleic acid of claim 1.

7. A transgenic *Jatropha curcas* plant cell, plant or plant seed comprising the isolated nucleic acid of claim 1 stably integrated into its genome,
  wherein said transgenic *Jatropha curcas* plant cell, plant or plant seed is obtained by *Agrobacterium*-meditated transformation.

8. A method for producing a transgenic *Jatropha curcas* plant which comprises introducing the isolated nucleic acid of claim 1 or an expression vector comprising the isolated nucleic acid of claim 1 into a *Jatropha curcas* plant, wherein the transgenic *Jatropha curcas* plant has the nucleic acid stably integrated in its genome and expresses the nucleic acid, and
  wherein said transgenic *Jatropha curcas* plant is obtained by *Agrobacterium*-meditated transformation.

9. A method for producing a transgenic *Jatropha curcas* plant which comprises transfecting the isolated nucleic acid of claim 1 or an expression vector comprising the isolated nucleic acid of claim 1 into a *Jatropha curcas* plant cell or *Jatropha curcas* plant cells and regenerating a transgenic *Jatropha curcas* plant from the transfected *Jatropha curcas* plant cell or transfected *Jatropha curcas* plant cells, wherein the transgenic *Jatropha curcas* plant has the nucleic acid stably integrated in its genome and expresses the nucleic acid; and
  wherein said transgenic *Jatropha curcas* plant is obtained by *Agrobacterium*-meditated transformation.

10. An isolated protein having the amino acid sequence set forth in SEQ ID NO:12.

11. The isolated nucleic acid of claim 3, wherein the promoter is heterologous to the nucleic acid.

12. An expression vector comprising the nucleic acid molecule of claim 2.

13. An expression vector comprising the isolated nucleic acid of claim 3.

14. An expression vector comprising the isolated nucleic acid of claim 11.

15. A transgenic *Jatropha curcas* plant cell, plant or plant seed comprising the nucleic acid molecule of claim 2 stably integrated into its genome,
  wherein said transgenic *Jatropha curcas* plant cell, plant or plant seed is obtained by *Agrobacterium*-meditated transformation.

16. A transgenic *Jatropha curcas* plant cell, plant or plant seed comprising the isolated nucleic acid of claim 3 stably integrated into its genome,
  wherein said transgenic *Jatropha curcas* plant cell, plant or plant seed is obtained by *Agrobacterium*-meditated transformation.

17. A transgenic *Jatropha curcas* plant cell, plant or plant seed comprising the isolated nucleic acid of claim 11 stably integrated into its genome,
  wherein said transgenic *Jatropha curcas* plant cell, plant or plant seed is obtained by *Agrobacterium*-meditated transformation.

18. A method for producing a transgenic *Jatropha curcas* plant which comprises introducing the nucleic acid molecule of claim 2 or an expression vector comprising the nucleic acid molecule of claim 2 into a *Jatropha curcas* plant, wherein the transgenic *Jatropha curcas* plant has the nucleic acid molecule stably integrated in its genome and expresses the nucleic acid,
  wherein said transgenic *Jatropha curcas* plant is obtained by *Agrobacterium*-meditated transformation.

19. A method for producing a transgenic *Jatropha curcas* plant which comprises introducing the isolated nucleic acid of claim 3 or an expression vector comprising the isolated nucleic acid of claim 3 into a *Jatropha curcas* plant, wherein the transgenic *Jatropha curcas* plant has the nucleic acid stably integrated in its genome and expresses the nucleic acid,
    wherein said transgenic *Jatropha curcas* plant is obtained by *Agrobacterium*-meditated transformation.

20. A method for producing a transgenic *Jatropha curcas* plant which comprises introducing the isolated nucleic acid of claim 11 or an expression vector comprising the isolated nucleic acid of claim 11 into a *Jatropha curcas* plant, wherein the transgenic *Jatropha curcas* plant has the nucleic acid stably integrated in its genome and expresses the nucleic acid,
    wherein said transgenic *Jatropha curcas* plant is obtained by *Agrobacterium*-meditated transformation.

21. A method for producing a transgenic *Jatropha curcas* plant which comprises transfecting the nucleic acid molecule of claim 2 or an expression vector comprising the nucleic acid molecule of claim 2 into a *Jatropha curcas* plant cell or *Jatropha curcas* plant cells and regenerating a transgenic *Jatropha curcas* plant from the transfected *Jatropha curcas* plant cell or transfected *Jatropha curcas* plant cells, wherein the transgenic *Jatropha curcas* plant has the nucleic acid molecule stably integrated in its genome and expresses the nucleic acid,
    wherein said transgenic *Jatropha curcas* plant is obtained by *Agrobacterium*-meditated transformation.

22. A method for producing a transgenic *Jatropha curcas* plant which comprises transfecting the isolated nucleic acid of claim 3 or an expression vector comprising the isolated nucleic acid of claim 3 into a *Jatropha curcas* plant cell or *Jatropha curcas* plant cells and regenerating a transgenic *Jatropha curcas* plant from the transfected *Jatropha curcas* plant cell or transfected *Jatropha curcas* plant cells, wherein the transgenic *Jatropha curcas* plant has the nucleic acid stably integrated in its genome and expresses the nucleic acid,
    wherein said transgenic *Jatropha curcas* plant is obtained by *Agrobacterium*-meditated transformation.

23. A method for producing a transgenic *Jatropha curcas* plant which comprises transfecting the isolated nucleic acid of claim 11 or an expression vector comprising the isolated nucleic acid of claim 11 into a *Jatropha curcas* plant cell or *Jatropha curcas* plant cells and regenerating a transgenic *Jatropha curcas* plant from the transfected *Jatropha curcas* plant cell or transfected *Jatropha curcas* plant cells, wherein the transgenic *Jatropha curcas* plant has the nucleic acid stably integrated in its genome and expresses the nucleic acid,
    wherein said transgenic *Jatropha curcas* plant is obtained by *Agrobacterium*-meditated transformation.

\* \* \* \* \*

SEQUENCE LISTING

```
<160> NUMBER OF SEQ ID NOS: 16

<210> SEQ ID NO 1
<211> LENGTH: 30
<212> TYPE: DNA
<213> ORGANISM: Jatropha curcas

<400> SEQUENCE: 1
aatcggatcc taatgaagag gtcttctgct                                        30

<210> SEQ ID NO 2
<211> LENGTH: 36
```

```
<212> TYPE: DNA
<213> ORGANISM: Jatropha curcas

<400> SEQUENCE: 2
tcatgttaat taatcaaaca gaatagttac aagaaa                        36

<210> SEQ ID NO 3
<211> LENGTH: 34
<212> TYPE: DNA
<213> ORGANISM: Jatropha curcas

<400> SEQUENCE: 3
caatatctag accatgacga ttttggagac cact                          34

<210> SEQ ID NO 4
<211> LENGTH: 30
<212> TYPE: DNA
<213> ORGANISM: Jatropha curcas

<400> SEQUENCE: 4
tattagatct ggtcttaatt cagcattgcc                               30

<210> SEQ ID NO 5
<211> LENGTH: 29
<212> TYPE: DNA
<213> ORGANISM: Ricinus communis

<400> SEQUENCE: 5
caatatctag accatgggag gtggtggtc                                29

<210> SEQ ID NO 6
<211> LENGTH: 31
<212> TYPE: DNA
<213> ORGANISM: Ricinus communis

<400> SEQUENCE: 6
tgtaggatcc ggatacttgt tccggtacca g                             31

<210> SEQ ID NO 7
<211> LENGTH: 18
<212> TYPE: DNA
<213> ORGANISM: Escherichia coli

<400> SEQUENCE: 7
cgatgtagga gggcgtgg                                            18

<210> SEQ ID NO 8
<211> LENGTH: 22
<212> TYPE: DNA
<213> ORGANISM: Escherichia coli

<400> SEQUENCE: 8
acttctacac agccatcggt cc                                       22

<210> SEQ ID NO 9
<211> LENGTH: 19
<212> TYPE: DNA
<213> ORGANISM: Streptomyces hygroscopicus

<400> SEQUENCE: 9
gtctgcacca tcgtcaacc                                           19

<210> SEQ ID NO 10
<211> LENGTH: 20
```

-continued

```
<212> TYPE: DNA
<213> ORGANISM: Streptomyces hygroscopicus

<400> SEQUENCE: 10
gaagtccagc tgccagaaac                                                  20

<210> SEQ ID NO 11
<211> LENGTH: 1251
<212> TYPE: DNA
<213> ORGANISM: Jatropha curcas
<220> FEATURE:
<221> NAME/KEY: CDS
<222> LOCATION: (1)..(1251)
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t

<400> SEQUENCE: 11
```

| | | | | | | | | | | | | | | | | |
|---|---|---|---|---|---|---|---|---|---|---|---|---|---|---|---|---|
| atg | aag | agg | tct | tct | gct | tca | tct | tgc | tct | tct | tct | tct | tct | tct | | 48 |
| Met | Lys | Arg | Ser | Ser | Ala | Ser | Ser | Cys | Ser | Ser | Ser | Ser | Ser | Ser | | |
| 1 | | | | 5 | | | | | 10 | | | | | 15 | | |
| tct | tct | cca | tcc | tct | tct | tcg | tct | tct | gct | tgt | tct | gct | tcg | tct | tct | 96 |
| Ser | Ser | Pro | Ser | Ser | Ser | Ser | Ser | Ser | Ala | Cys | Ser | Ala | Ser | Ser | Ser | |
| | | 20 | | | | | 25 | | | | | 30 | | | | |
| tgc | tta | gat | tca | gta | tct | cct | cct | aat | cac | cat | caa | tta | cga | tca | gag | 144 |
| Cys | Leu | Asp | Ser | Val | Ser | Pro | Pro | Asn | His | His | Gln | Leu | Arg | Ser | Glu | |
| | 35 | | | | | 40 | | | | | 45 | | | | | |
| aaa | tca | aaa | tcc | aaa | cgc | att | cga | aaa | att | caa | acc | aag | caa | gat | aaa | 192 |
| Lys | Ser | Lys | Ser | Lys | Arg | Ile | Arg | Lys | Ile | Gln | Thr | Lys | Gln | Asp | Lys | |
| 50 | | | | | 55 | | | | | 60 | | | | | | |
| tgt | cag | act | aca | gct | act | acc | acc | agt | cca | agc | ggc | ggc | ggt | agg | aga | 240 |
| Cys | Gln | Thr | Thr | Ala | Thr | Thr | Thr | Ser | Pro | Ser | Gly | Gly | Gly | Arg | Arg | |
| 65 | | | | 70 | | | | | 75 | | | | | 80 | | |
| agc | tcc | att | tac | aga | gga | gtc | acc | cgg | cat | aga | tgg | act | gga | agg | ttt | 288 |
| Ser | Ser | Ile | Tyr | Arg | Gly | Val | Thr | Arg | His | Arg | Trp | Thr | Gly | Arg | Phe | |
| | | | | 85 | | | | | 90 | | | | | 95 | | |
| gaa | gct | cat | ctt | tgg | gat | aag | agt | tct | tgg | aat | aac | att | caa | aac | aag | 336 |
| Glu | Ala | His | Leu | Trp | Asp | Lys | Ser | Ser | Trp | Asn | Asn | Ile | Gln | Asn | Lys | |
| | | | 100 | | | | | 105 | | | | | 110 | | | |
| aaa | gga | agg | caa | gtt | tat | ttg | ggg | gct | tac | gac | aat | gag | gaa | gca | gct | 384 |
| Lys | Gly | Arg | Gln | Val | Tyr | Leu | Gly | Ala | Tyr | Asp | Asn | Glu | Glu | Ala | Ala | |
| | | 115 | | | | | 120 | | | | | 125 | | | | |
| gct | cat | acc | tat | gat | ctt | gct | gct | ctc | aag | tac | tgg | gga | caa | gac | acc | 432 |
| Ala | His | Thr | Tyr | Asp | Leu | Ala | Ala | Leu | Lys | Tyr | Trp | Gly | Gln | Asp | Thr | |
| | 130 | | | | | 135 | | | | | 140 | | | | | |
| act | ttg | aat | ttt | ccg | ata | gag | aca | tac | tca | aag | gag | ctt | gaa | gag | atg | 480 |
| Thr | Leu | Asn | Phe | Pro | Ile | Glu | Thr | Tyr | Ser | Lys | Glu | Leu | Glu | Glu | Met | |
| 145 | | | | | 150 | | | | | 155 | | | | | 160 | |
| caa | aag | atg | agc | aag | gaa | gag | tac | tta | gca | tct | ctt | cna | cgg | aga | agc | 528 |
| Gln | Lys | Met | Ser | Lys | Glu | Glu | Tyr | Leu | Ala | Ser | Leu | Xaa | Arg | Arg | Ser | |
| | | | | 165 | | | | | 170 | | | | | 175 | | |
| agt | gga | ttt | tca | aga | gga | gtt | tct | aag | tac | cgg | gga | gta | gct | agg | cat | 576 |
| Ser | Gly | Phe | Ser | Arg | Gly | Val | Ser | Lys | Tyr | Arg | Gly | Val | Ala | Arg | His | |
| | | | 180 | | | | | 185 | | | | | 190 | | | |
| cat | cac | aat | ggc | cgg | tgg | gaa | gct | cga | att | ggc | cgg | gtt | ttt | ggc | aat | 624 |
| His | His | Asn | Gly | Arg | Trp | Glu | Ala | Arg | Ile | Gly | Arg | Val | Phe | Gly | Asn | |
| | | 195 | | | | | 200 | | | | | 205 | | | | |
| aag | tat | ctc | tac | ctc | gga | act | tac | aat | aca | caa | gaa | gag | gca | gca | gca | 672 |
| Lys | Tyr | Leu | Tyr | Leu | Gly | Thr | Tyr | Asn | Thr | Gln | Glu | Glu | Ala | Ala | Ala | |

```
tat gat atg gca gca ata gag tac aga gga gca aat gca gta acc aat      720
Tyr Asp Met Ala Ala Ile Glu Tyr Arg Gly Ala Asn Ala Val Thr Asn
225                 230                 235                 240 ttt gat gtc agc cat tac ata gac cgt ttg aag aag aaa ggc att cct      768
Phe Asp Val Ser His Tyr Ile Asp Arg Leu Lys Lys Lys Gly Ile Pro
                245                 250                 255 tta gat aaa atc cta cca gaa acn ctt tct aaa ggc tca aaa gag tca      816
Leu Asp Lys Ile Leu Pro Glu Thr Leu Ser Lys Gly Ser Lys Glu Ser
            260                 265                 270 gaa gaa atc gag cga acc tca ccc tta ccg ttg cca tca cca cca tca      864
Glu Glu Ile Glu Arg Thr Ser Pro Leu Pro Leu Pro Ser Pro Pro Ser
        275                 280                 285 cca tca ata aca cca tta cac gaa gaa ata gtc tca cca cag ctg ctt      912
Pro Ser Ile Thr Pro Leu His Glu Glu Ile Val Ser Pro Gln Leu Leu
    290                 295                 300 gaa act gaa tgc cca caa cat cct cca tgt atg gat act tgt act atg      960
Glu Thr Glu Cys Pro Gln His Pro Pro Cys Met Asp Thr Cys Thr Met
305                 310                 315                 320 atc gtt atg gac cct ata gaa gag cac gag ctt act tgg agc ttc tgt     1008
Ile Val Met Asp Pro Ile Glu Glu His Glu Leu Thr Trp Ser Phe Cys
                325                 330                 335 ctc gat tcg ggg tta gtt ccg ctc cct gtg cct gac cta cca cta gca     1056
Leu Asp Ser Gly Leu Val Pro Leu Pro Val Pro Asp Leu Pro Leu Ala
            340                 345                 350 aat ggc tgt gag tta cca gac ttg ttg gat gac aca ggc ttt gaa gac     1104
Asn Gly Cys Glu Leu Pro Asp Leu Leu Asp Asp Thr Gly Phe Glu Asp
        355                 360                 365 aat att gac ttg ata ttt gat gct tgt tgc ttc gga aat gat gcc aac     1152
Asn Ile Asp Leu Ile Phe Asp Ala Cys Cys Phe Gly Asn Asp Ala Asn
    370                 375                 380 cct gca gat gag aat ggg aaa gag agg ttg tct tcc gct tca act tct     1200
Pro Ala Asp Glu Asn Gly Lys Glu Arg Leu Ser Ser Ala Ser Thr Ser
385                 390                 395                 400 cca tct tgt tcc aca aca tta act tct gtt tct tgt aac tat tct gtt     1248
Pro Ser Cys Ser Thr Thr Leu Thr Ser Val Ser Cys Asn Tyr Ser Val
                405                 410                 415 tga                                                                  1251

<210> SEQ ID NO 12
<211> LENGTH: 416
<212> TYPE: PRT
<213> ORGANISM: Jatropha curcas
<220> FEATURE:
<221> NAME/KEY: misc_feature
<222> LOCATION: (173)..(173)
<223> OTHER INFORMATION: The 'Xaa' at location 173 stands for Gln, Arg,
      Pro, or Leu.

<400> SEQUENCE: 12

Met Lys Arg Ser Ser Ala Ser Ser Cys Ser Ser Ser Ser Ser Ser Ser
1               5                   10                  15

Ser Ser Pro Ser Ser Ser Ser Ser Ala Cys Ser Ala Ser Ser Ser
            20                  25                  30

Cys Leu Asp Ser Val Ser Pro Pro Asn His His Gln Leu Arg Ser Glu
        35                  40                  45

Lys Ser Lys Ser Lys Arg Ile Arg Lys Ile Gln Thr Lys Gln Asp Lys
    50                  55                  60

Cys Gln Thr Thr Ala Thr Thr Thr Ser Pro Ser Gly Gly Gly Arg Arg
65                  70                  75                  80
```

```
Ser Ser Ile Tyr Arg Gly Val Thr Arg His Arg Trp Thr Gly Arg Phe
                85                  90                  95
Glu Ala His Leu Trp Asp Lys Ser Ser Trp Asn Asn Ile Gln Asn Lys
            100                 105                 110
Lys Gly Arg Gln Val Tyr Leu Gly Ala Tyr Asp Asn Glu Glu Ala Ala
        115                 120                 125
Ala His Thr Tyr Asp Leu Ala Ala Leu Lys Tyr Trp Gly Gln Asp Thr
    130                 135                 140
Thr Leu Asn Phe Pro Ile Glu Thr Tyr Ser Lys Glu Leu Glu Glu Met
145                 150                 155                 160
Gln Lys Met Ser Lys Glu Glu Tyr Leu Ala Ser Leu Xaa Arg Arg Ser
                165                 170                 175
Ser Gly Phe Ser Arg Gly Val Ser Lys Tyr Arg Gly Val Ala Arg His
            180                 185                 190
His His Asn Gly Arg Trp Glu Ala Arg Ile Gly Arg Val Phe Gly Asn
        195                 200                 205
Lys Tyr Leu Tyr Leu Gly Thr Tyr Asn Thr Gln Glu Glu Ala Ala Ala
    210                 215                 220
Tyr Asp Met Ala Ala Ile Glu Tyr Arg Gly Ala Asn Ala Val Thr Asn
225                 230                 235                 240
Phe Asp Val Ser His Tyr Ile Asp Arg Leu Lys Lys Lys Gly Ile Pro
                245                 250                 255
Leu Asp Lys Ile Leu Pro Glu Thr Leu Ser Lys Gly Ser Lys Glu Ser
            260                 265                 270
Glu Glu Ile Glu Arg Thr Ser Pro Leu Pro Leu Pro Ser Pro Pro Ser
        275                 280                 285
Pro Ser Ile Thr Pro Leu His Glu Gly Ile Val Ser Pro Gln Leu Leu
    290                 295                 300
Glu Thr Glu Cys Pro Gln His Pro Pro Cys Met Asp Thr Cys Thr Met
305                 310                 315                 320
Ile Val Met Asp Pro Ile Glu Glu His Glu Leu Thr Trp Ser Phe Cys
                325                 330                 335
Leu Asp Ser Gly Leu Val Pro Leu Pro Val Pro Asp Leu Pro Leu Ala
            340                 345                 350
Asn Gly Cys Glu Leu Pro Asp Leu Leu Asp Asp Thr Gly Phe Glu Asp
        355                 360                 365
Asn Ile Asp Leu Ile Phe Asp Ala Cys Cys Phe Gly Asn Asp Ala Asn
    370                 375                 380
Pro Ala Asp Glu Asn Gly Lys Glu Arg Leu Ser Ser Ala Ser Thr Ser
385                 390                 395                 400
Pro Ser Cys Ser Thr Thr Leu Thr Ser Val Ser Cys Asn Tyr Ser Val
                405                 410                 415

<210> SEQ ID NO 13
<211> LENGTH: 1566
<212> TYPE: DNA
<213> ORGANISM: Jatropha curcas
<220> FEATURE:
<221> NAME/KEY: CDS
<222> LOCATION: (1)..(1566)

<400> SEQUENCE: 13 atg acg att ttg gag acc act act agc gga ggt gat ggt gtt gct gag     48
Met Thr Ile Leu Glu Thr Thr Thr Ser Gly Gly Asp Gly Val Ala Glu
1               5                   10                  15 tcg tct tcc gat ctt aac gta tcg ctt cga cgg aga cgg aaa ggc acc     96
Ser Ser Ser Asp Leu Asn Val Ser Leu Arg Arg Arg Arg Lys Gly Thr
```

```
                 20                  25                  30
agc tcg gat gga gct ttg ccg gaa ttg act tcg aat att gtt gaa ttg      144
Ser Ser Asp Gly Ala Leu Pro Glu Leu Thr Ser Asn Ile Val Glu Leu
         35                  40                  45 gaa tct gaa agc ggt ggc cag gtg atg atg gat cca ggt gtg gtg acg      192
Glu Ser Glu Ser Gly Gly Gln Val Met Met Asp Pro Gly Val Val Thr
 50                  55                  60 gaa ccg gag aca gag aaa att aat gga aaa gat tgc ggc ggt gac aag      240
Glu Pro Glu Thr Glu Lys Ile Asn Gly Lys Asp Cys Gly Gly Asp Lys
 65                  70                  75                  80 gat aag att gac aat cgc gag aat cgt ggg agg tcg gat att aaa ttc      288
Asp Lys Ile Asp Asn Arg Glu Asn Arg Gly Arg Ser Asp Ile Lys Phe
                 85                  90                  95 acg tac cgg cca tcg gtg ccg gct cat cga gcg ctc agg gag agt ccg      336
Thr Tyr Arg Pro Ser Val Pro Ala His Arg Ala Leu Arg Glu Ser Pro
            100                 105                 110 ctt agc tct gat gct ata ttt aaa caa agt cat gca ggt ctg ttc aac      384
Leu Ser Ser Asp Ala Ile Phe Lys Gln Ser His Ala Gly Leu Phe Asn
        115                 120                 125 ctc tgt ata gta gtg ctt gtt gct gtt aac agc agg ctt atc att gaa      432
Leu Cys Ile Val Val Leu Val Ala Val Asn Ser Arg Leu Ile Ile Glu
    130                 135                 140 aat cta atg aag tac ggt tgg tta att aaa acg ggg ttt tgg ttt agt      480
Asn Leu Met Lys Tyr Gly Trp Leu Ile Lys Thr Gly Phe Trp Phe Ser
145                 150                 155                 160 tca aga tcg ttg aga gat tgg ccc ctt ctt atg tgc tgt ctt acc ctc      528
Ser Arg Ser Leu Arg Asp Trp Pro Leu Leu Met Cys Cys Leu Thr Leu
                165                 170                 175 cct ata ttc tct ctt gcc gcc tat cta gtt gag aag ttg gca tat cga      576
Pro Ile Phe Ser Leu Ala Ala Tyr Leu Val Glu Lys Leu Ala Tyr Arg
            180                 185                 190 aaa tat ata tct gca cct att gtt att ttc ttt cat atg ctc att acc      624
Lys Tyr Ile Ser Ala Pro Ile Val Ile Phe Phe His Met Leu Ile Thr
        195                 200                 205 aca aca gca gtt ttg tac cca gtt tct gtg att ctc agt tgt ggg tct      672
Thr Thr Ala Val Leu Tyr Pro Val Ser Val Ile Leu Ser Cys Gly Ser
    210                 215                 220 gct gtt ctg tct ggt gtt gca ttg atg ctc ttt gct tgt atc gtg tgg      720
Ala Val Leu Ser Gly Val Ala Leu Met Leu Phe Ala Cys Ile Val Trp
225                 230                 235                 240 ttg aaa tta gta tct tat gca cat aca aac tat gac atg aga gcc att      768
Leu Lys Leu Val Ser Tyr Ala His Thr Asn Tyr Asp Met Arg Ala Ile
                245                 250                 255 gcc aac tca gct gac aag gga gat gca cta tcc gat act tca ggt gca      816
Ala Asn Ser Ala Asp Lys Gly Asp Ala Leu Ser Asp Thr Ser Gly Ala
            260                 265                 270 gat tct tca cgt gat gtt agc ttc aag agt ttg gtc tac ttc atg gtt      864
Asp Ser Ser Arg Asp Val Ser Phe Lys Ser Leu Val Tyr Phe Met Val
        275                 280                 285 gct cct acg cta tgt tac cag cca agt tat cct cga aca gat tca gtt      912
Ala Pro Thr Leu Cys Tyr Gln Pro Ser Tyr Pro Arg Thr Asp Ser Val
    290                 295                 300 aga aag ggt tgg gtg gtt cgt caa ttt gtc aag tta ata ata ttt aca      960
Arg Lys Gly Trp Val Val Arg Gln Phe Val Lys Leu Ile Ile Phe Thr
305                 310                 315                 320 gga ttc atg gga ttt atc ata gaa caa tat atc aat cct att gtc cag     1008
Gly Phe Met Gly Phe Ile Ile Glu Gln Tyr Ile Asn Pro Ile Val Gln
                325                 330                 335 aat tca caa cat ccc tta aag ggg gat cta tta tat gcc att gaa agg     1056
Asn Ser Gln His Pro Leu Lys Gly Asp Leu Leu Tyr Ala Ile Glu Arg
```

```
                     340                 345                 350
gtt ttg aag ctc tca gtt cca aac tta tat gtg tgg ctt tgc atg ttc     1104
Val Leu Lys Leu Ser Val Pro Asn Leu Tyr Val Trp Leu Cys Met Phe
        355                 360                 365 tac tgc ttt ttt cat cta tgg tta aat ata ctt gct gag ctc ctt cgg     1152
Tyr Cys Phe Phe His Leu Trp Leu Asn Ile Leu Ala Glu Leu Leu Arg
    370                 375                 380 ttt ggt gac aga gag ttc tat aaa gat tgg tgg aat gca agg acc gtt     1200
Phe Gly Asp Arg Glu Phe Tyr Lys Asp Trp Trp Asn Ala Arg Thr Val
385                 390                 395                 400 gag gag tac tgg aga atg tgg aat atg cct gtt cat aag tgg atg gtt     1248
Glu Glu Tyr Trp Arg Met Trp Asn Met Pro Val His Lys Trp Met Val
                405                 410                 415 cgc cat atc tac ttt cca tgc ttg cgg cat aaa ata cca agg ggg gta     1296
Arg His Ile Tyr Phe Pro Cys Leu Arg His Lys Ile Pro Arg Gly Val
            420                 425                 430 gcc ttg tta att gct ttc ttc gtt tca gct gta ttt cat gag ttg tgc     1344
Ala Leu Leu Ile Ala Phe Phe Val Ser Ala Val Phe His Glu Leu Cys
        435                 440                 445 att gct gtt cct tgc cac atg ttc aag ctc tgg gct ttt att gga att     1392
Ile Ala Val Pro Cys His Met Phe Lys Leu Trp Ala Phe Ile Gly Ile
450                 455                 460 atg ttt cag att cca ttg gtc ggg atc act aat tac ctc cag aac aag     1440
Met Phe Gln Ile Pro Leu Val Gly Ile Thr Asn Tyr Leu Gln Asn Lys
465                 470                 475                 480 ttc aga agc tcc atg gtg gga aat atg atc ttt tgg ttc att ttc tgc     1488
Phe Arg Ser Ser Met Val Gly Asn Met Ile Phe Trp Phe Ile Phe Cys
                485                 490                 495 att ctt ggt caa ccc atg tgt gtg cta ttg tat tat cat gac cta atg     1536
Ile Leu Gly Gln Pro Met Cys Val Leu Leu Tyr Tyr His Asp Leu Met
            500                 505                 510 aat cgg aaa ggc aat gct gaa tta aga tga                             1566
Asn Arg Lys Gly Asn Ala Glu Leu Arg
        515                 520

<210> SEQ ID NO 14
<211> LENGTH: 521
<212> TYPE: PRT
<213> ORGANISM: Jatropha curcas

<400> SEQUENCE: 14

Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Val Val Thr
    50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
        115                 120                 125

Leu Cys Ile Val Val Leu Val Ala Val Asn Ser Arg Leu Ile Ile Glu
    130                 135                 140
```

```
Asn Leu Met Lys Tyr Gly Trp Leu Ile Lys Thr Gly Phe Trp Phe Ser
145                 150                 155                 160

Ser Arg Ser Leu Arg Asp Trp Pro Leu Leu Met Cys Cys Leu Thr Leu
            165                 170                 175

Pro Ile Phe Ser Leu Ala Ala Tyr Leu Val Glu Lys Leu Ala Tyr Arg
        180                 185                 190

Lys Tyr Ile Ser Ala Pro Ile Val Ile Phe Phe His Met Leu Ile Thr
        195                 200                 205

Thr Thr Ala Val Leu Tyr Pro Val Ser Val Ile Leu Ser Cys Gly Ser
    210                 215                 220

Ala Val Leu Ser Gly Val Ala Leu Met Leu Phe Ala Cys Ile Val Trp
225                 230                 235                 240

Leu Lys Leu Val Ser Tyr Ala His Thr Asn Tyr Asp Met Arg Ala Ile
            245                 250                 255

Ala Asn Ser Ala Asp Lys Gly Asp Ala Leu Ser Asp Thr Ser Gly Ala
        260                 265                 270

Asp Ser Ser Arg Asp Val Ser Phe Lys Ser Leu Val Tyr Phe Met Val
        275                 280                 285

Ala Pro Thr Leu Cys Tyr Gln Pro Ser Tyr Pro Arg Thr Asp Ser Val
    290                 295                 300

Arg Lys Gly Trp Val Val Arg Gln Phe Val Lys Leu Ile Ile Phe Thr
305                 310                 315                 320

Gly Phe Met Gly Phe Ile Ile Glu Gln Tyr Ile Asn Pro Ile Val Gln
            325                 330                 335

Asn Ser Gln His Pro Leu Lys Gly Asp Leu Leu Tyr Ala Ile Glu Arg
        340                 345                 350

Val Leu Lys Leu Ser Val Pro Asn Leu Tyr Val Trp Leu Cys Met Phe
        355                 360                 365

Tyr Cys Phe Phe His Leu Trp Leu Asn Ile Leu Ala Glu Leu Leu Arg
    370                 375                 380

Phe Gly Asp Arg Glu Phe Tyr Lys Asp Trp Trp Asn Ala Arg Thr Val
385                 390                 395                 400

Glu Glu Tyr Trp Arg Met Trp Asn Met Pro Val His Lys Trp Met Val
            405                 410                 415

Arg His Ile Tyr Phe Pro Cys Leu Arg His Lys Ile Pro Arg Gly Val
        420                 425                 430

Ala Leu Leu Ile Ala Phe Phe Val Ser Ala Val Phe His Glu Leu Cys
        435                 440                 445

Ile Ala Val Pro Cys His Met Phe Lys Leu Trp Ala Phe Ile Gly Ile
    450                 455                 460

Met Phe Gln Ile Pro Leu Val Gly Ile Thr Asn Tyr Leu Gln Asn Lys
465                 470                 475                 480

Phe Arg Ser Ser Met Val Gly Asn Met Ile Phe Trp Phe Ile Phe Cys
            485                 490                 495

Ile Leu Gly Gln Pro Met Cys Val Leu Leu Tyr Tyr His Asp Leu Met
        500                 505                 510

Asn Arg Lys Gly Asn Ala Glu Leu Arg
        515                 520

<210> SEQ ID NO 15
<211> LENGTH: 1164
<212> TYPE: DNA
<213> ORGANISM: Ricinus communis
<220> FEATURE:
<221> NAME/KEY: CDS
```

<222> LOCATION: (1)..(1164)

<400> SEQUENCE: 15

| | | | | | | | | | | | | | | | | |
|---|---|---|---|---|---|---|---|---|---|---|---|---|---|---|---|---|
| atg | gga | ggt | ggt | ggt | cgc | atg | tct | act | gtc | ata | acc | agc | aac | aac | agt | 48 |
| Met | Gly | Gly | Gly | Gly | Arg | Met | Ser | Thr | Val | Ile | Thr | Ser | Asn | Asn | Ser | |
| 1 | | | | 5 | | | | | 10 | | | | | 15 | | |

| gag | aag | aaa | gga | gga | agc | agc | cac | ctt | aag | cga | gcg | ccg | cac | acg | aag | 96 |
|---|---|---|---|---|---|---|---|---|---|---|---|---|---|---|---|---|
| Glu | Lys | Lys | Gly | Gly | Ser | Ser | His | Leu | Lys | Arg | Ala | Pro | His | Thr | Lys | |
| | | | 20 | | | | | 25 | | | | | 30 | | | |

| cct | cct | ttc | aca | ctt | ggt | gac | ctc | aag | aga | gcc | atc | cca | ccc | cat | tgc | 144 |
|---|---|---|---|---|---|---|---|---|---|---|---|---|---|---|---|---|
| Pro | Pro | Phe | Thr | Leu | Gly | Asp | Leu | Lys | Arg | Ala | Ile | Pro | Pro | His | Cys | |
| | | 35 | | | | | 40 | | | | | 45 | | | | |

| ttt | gaa | cgc | tct | ttt | gtg | cgc | tca | ttc | tcc | tat | gtt | gcc | tat | gat | gtc | 192 |
|---|---|---|---|---|---|---|---|---|---|---|---|---|---|---|---|---|
| Phe | Glu | Arg | Ser | Phe | Val | Arg | Ser | Phe | Ser | Tyr | Val | Ala | Tyr | Asp | Val | |
| 50 | | | | | 55 | | | | | 60 | | | | | | |

| tgc | tta | agt | ttt | ctt | ttc | tac | tcg | atc | gcc | acc | aac | ttc | ttc | cct | tac | 240 |
|---|---|---|---|---|---|---|---|---|---|---|---|---|---|---|---|---|
| Cys | Leu | Ser | Phe | Leu | Phe | Tyr | Ser | Ile | Ala | Thr | Asn | Phe | Phe | Pro | Tyr | |
| 65 | | | | 70 | | | | | 75 | | | | | 80 | | |

| atc | tct | tct | ccg | ctc | tcg | tat | gtc | gct | tgg | ctg | gtt | tac | tgg | ctc | ttc | 288 |
|---|---|---|---|---|---|---|---|---|---|---|---|---|---|---|---|---|
| Ile | Ser | Ser | Pro | Leu | Ser | Tyr | Val | Ala | Trp | Leu | Val | Tyr | Trp | Leu | Phe | |
| | | | | 85 | | | | | 90 | | | | | 95 | | |

| caa | ggc | tgc | att | ctc | act | ggt | ctt | tgg | gtc | atc | ggc | cat | gaa | tgt | ggc | 336 |
|---|---|---|---|---|---|---|---|---|---|---|---|---|---|---|---|---|
| Gln | Gly | Cys | Ile | Leu | Thr | Gly | Leu | Trp | Val | Ile | Gly | His | Glu | Cys | Gly | |
| | | | 100 | | | | | 105 | | | | | 110 | | | |

| cat | cat | gct | ttt | agt | gag | tat | cag | ctg | gct | gat | gac | att | gtt | ggc | cta | 384 |
|---|---|---|---|---|---|---|---|---|---|---|---|---|---|---|---|---|
| His | His | Ala | Phe | Ser | Glu | Tyr | Gln | Leu | Ala | Asp | Asp | Ile | Val | Gly | Leu | |
| | | 115 | | | | | 120 | | | | | 125 | | | | |

| att | gtc | cat | tct | gca | ctt | ctg | gtt | cca | tat | ttt | tca | tgg | aaa | tat | agc | 432 |
|---|---|---|---|---|---|---|---|---|---|---|---|---|---|---|---|---|
| Ile | Val | His | Ser | Ala | Leu | Leu | Val | Pro | Tyr | Phe | Ser | Trp | Lys | Tyr | Ser | |
| 130 | | | | | 135 | | | | | 140 | | | | | | |

| cat | cgc | cgc | cac | cat | tct | aac | ata | gga | tct | ctc | gag | cga | gac | gaa | gtg | 480 |
|---|---|---|---|---|---|---|---|---|---|---|---|---|---|---|---|---|
| His | Arg | Arg | His | His | Ser | Asn | Ile | Gly | Ser | Leu | Glu | Arg | Asp | Glu | Val | |
| 145 | | | | | 150 | | | | | 155 | | | | | 160 | |

| ttc | gtc | ccg | aaa | tca | aag | tcg | aaa | att | tca | tgg | tat | tct | aag | tac | tca | 528 |
|---|---|---|---|---|---|---|---|---|---|---|---|---|---|---|---|---|
| Phe | Val | Pro | Lys | Ser | Lys | Ser | Lys | Ile | Ser | Trp | Tyr | Ser | Lys | Tyr | Ser | |
| | | | | 165 | | | | | 170 | | | | | 175 | | |

| aac | aac | ccg | cca | ggt | cga | gtt | ttg | aca | ctt | gct | gcc | acg | ctc | ctc | ctt | 576 |
|---|---|---|---|---|---|---|---|---|---|---|---|---|---|---|---|---|
| Asn | Asn | Pro | Pro | Gly | Arg | Val | Leu | Thr | Leu | Ala | Ala | Thr | Leu | Leu | Leu | |
| | | | 180 | | | | | 185 | | | | | 190 | | | |

| ggc | tgg | cct | tta | tac | tta | gct | ttc | aat | gtc | tct | ggt | aga | cct | tac | gat | 624 |
|---|---|---|---|---|---|---|---|---|---|---|---|---|---|---|---|---|
| Gly | Trp | Pro | Leu | Tyr | Leu | Ala | Phe | Asn | Val | Ser | Gly | Arg | Pro | Tyr | Asp | |
| | | 195 | | | | | 200 | | | | | 205 | | | | |

| cgc | ttt | gct | tgc | cat | tat | gat | ccc | tat | ggc | cca | ata | ttt | tcc | gaa | aga | 672 |
|---|---|---|---|---|---|---|---|---|---|---|---|---|---|---|---|---|
| Arg | Phe | Ala | Cys | His | Tyr | Asp | Pro | Tyr | Gly | Pro | Ile | Phe | Ser | Glu | Arg | |
| | | 210 | | | | | 215 | | | | | 220 | | | | |

| gaa | agg | ctt | cag | att | tac | att | gct | gac | ctc | gga | atc | ttt | gcc | aca | acg | 720 |
|---|---|---|---|---|---|---|---|---|---|---|---|---|---|---|---|---|
| Glu | Arg | Leu | Gln | Ile | Tyr | Ile | Ala | Asp | Leu | Gly | Ile | Phe | Ala | Thr | Thr | |
| 225 | | | | | 230 | | | | | 235 | | | | | 240 | |

| ttt | gtg | ctt | tat | cag | gct | aca | atg | gca | aaa | ggg | ttg | gct | tgg | gta | atg | 768 |
|---|---|---|---|---|---|---|---|---|---|---|---|---|---|---|---|---|
| Phe | Val | Leu | Tyr | Gln | Ala | Thr | Met | Ala | Lys | Gly | Leu | Ala | Trp | Val | Met | |
| | | | | 245 | | | | | 250 | | | | | 255 | | |

| cgt | atc | tat | ggg | gtg | cca | ttg | ctt | att | gtt | aac | tgt | ttc | ctt | gtt | atg | 816 |
|---|---|---|---|---|---|---|---|---|---|---|---|---|---|---|---|---|
| Arg | Ile | Tyr | Gly | Val | Pro | Leu | Leu | Ile | Val | Asn | Cys | Phe | Leu | Val | Met | |
| | | | 260 | | | | | 265 | | | | | 270 | | | |

| atc | aca | tac | ttg | cag | cac | act | cac | cca | gct | att | cca | cgc | tat | ggc | tca | 864 |
|---|---|---|---|---|---|---|---|---|---|---|---|---|---|---|---|---|
| Ile | Thr | Tyr | Leu | Gln | His | Thr | His | Pro | Ala | Ile | Pro | Arg | Tyr | Gly | Ser | |
| | | 275 | | | | | 280 | | | | | 285 | | | | |

| tcg | gaa | tgg | gat | tgg | ctc | cgg | gga | gca | atg | gtg | act | gtc | gat | aga | gat | 912 |
|---|---|---|---|---|---|---|---|---|---|---|---|---|---|---|---|---|
| Ser | Glu | Trp | Asp | Trp | Leu | Arg | Gly | Ala | Met | Val | Thr | Val | Asp | Arg | Asp | |
| 290 | | | | | 295 | | | | | 300 | | | | | | |

```
tat ggg gtg ttg aat aaa gta ttc cat aac att gca gac act cat gta    960
Tyr Gly Val Leu Asn Lys Val Phe His Asn Ile Ala Asp Thr His Val
305                 310                 315                 320 gct cat cat ctc ttt gct aca gtg cca cat tac cat gca atg gag gcc   1008
Ala His His Leu Phe Ala Thr Val Pro His Tyr His Ala Met Glu Ala
                325                 330                 335 act aaa gca atc aag cct ata atg ggt gag tat tac cgg tat gat ggt   1056
Thr Lys Ala Ile Lys Pro Ile Met Gly Glu Tyr Tyr Arg Tyr Asp Gly
            340                 345                 350 acc cca ttt tac aag gca ttg tgg agg gag gca aag gag tgc ttg ttc   1104
Thr Pro Phe Tyr Lys Ala Leu Trp Arg Glu Ala Lys Glu Cys Leu Phe
        355                 360                 365 gtc gag cca gat gaa gga gct cct aca caa ggc gtt ttc tgg tac cgg   1152
Val Glu Pro Asp Glu Gly Ala Pro Thr Gln Gly Val Phe Trp Tyr Arg
370                 375                 380 aac aag tat taa                                                   1164
Asn Lys Tyr
385
```

```
            -continued

Arg Ile Tyr Gly Val Pro Leu Leu Ile Val Asn Cys Phe Leu Val Met
            260             265             270

Ile Thr Tyr Leu Gln His Thr His Pro Ala Ile Pro Arg Tyr Gly Ser
        275             280             285

Ser Glu Trp Asp Trp Leu Arg Gly Ala Met Val Thr Val Asp Arg Asp
    290             295             300

Tyr Gly Val Leu Asn Lys Val Phe His Asn Ile Ala Asp Thr His Val
305             310             315             320

Ala His His Leu Phe Ala Thr Val Pro His Tyr His Ala Met Glu Ala
            325             330             335

Thr Lys Ala Ile Lys Pro Ile Met Gly Glu Tyr Tyr Arg Tyr Asp Gly
            340             345             350

Thr Pro Phe Tyr Lys Ala Leu Trp Arg Glu Ala Lys Glu Cys Leu Phe
            355             360             365

Val Glu Pro Asp Glu Gly Ala Pro Thr Gln Gly Val Phe Trp Tyr Arg
    370             375             380

Asn Lys Tyr
385
```